United States Patent
Shurtleff

(10) Patent No.: US 9,629,777 B2
(45) Date of Patent: Apr. 25, 2017

(54) EXERCISE SAUNA HAVING FAR INFRARED HEATING ELEMENTS AND CONFIGURABLE SEATING

(71) Applicant: David Floyd Shurtleff, Palm Harbor, FL (US)

(72) Inventor: David Floyd Shurtleff, Palm Harbor, FL (US)

(73) Assignee: HI-Q HOLDINGS LLC

( * ) Notice: Subject to any disclaimer, the term of this patent is extended or adjusted under 35 U.S.C. 154(b) by 242 days.

(21) Appl. No.: 13/933,018

(22) Filed: Jul. 1, 2013

(65) Prior Publication Data

US 2014/0157511 A1    Jun. 12, 2014

Related U.S. Application Data

(60) Provisional application No. 61/666,839, filed on Jun. 30, 2012, provisional application No. 61/804,284, filed on Mar. 22, 2013.

(51) Int. Cl.
*A61H 33/06* (2006.01)
*A63B 21/04* (2006.01)
(Continued)

(52) U.S. Cl.
CPC ......... *A61H 33/063* (2013.01); *A61H 33/067* (2013.01); *A63B 21/0442* (2013.01); *A63B 21/0552* (2013.01); *A63B 21/16* (2013.01); *A63B 23/03541* (2013.01); *A61H 2201/10* (2013.01); *A61N 2005/064* (2013.01); *A61N 2005/066* (2013.01); *A61N 2005/0633* (2013.01); *A61N 2005/0668* (2013.01);
(Continued)

(58) Field of Classification Search
CPC ............ A61H 2033/061; A61H 33/063; A61H 33/66; A61H 33/67; A61H 33/06; A63B 21/0557
USPC ...................................... 4/524; 482/121–123
See application file for complete search history.

(56) References Cited

U.S. PATENT DOCUMENTS 3,313,916 A * 4/1967 Achner .................. A61H 33/06
219/385
5,188,099 A * 2/1993 Todeschini ............. A61H 33/06
128/202.12
(Continued)

*Primary Examiner* — Janie Loeppke
(74) *Attorney, Agent, or Firm* — Gary L. Eastman, Esq.; Eastman & McCartney LLP

(57) ABSTRACT

A far infrared ("FIR") sauna cabin equipped with a far infrared ("FIR") heating elements constructed of ceramic, carbon, and/or light emitting diodes ("LED"), designed for therapeutic use in a sauna, capable of emitting far infrared energy, and heating an individual's skin for purposes of rejuvenation, anti-aging, weight loss, and acne therapy. The FIR heating element emits IR energy in a wavelength and frequency optimum for resonant absorption by the human body, resulting in the release of toxins stored within subcutaneous fatty deposits, which are then carried out of the person's system as he or she sweats. The FIR sauna cabin is further equipped with necessary hardware and tools to effectively create a more flexible environment in which the user can change seating configurations, move about more freely and conduct stretching routines or exercises within the sauna cabin, using specialized fittings integrated to the interior of the sauna cabin.

20 Claims, 15 Drawing Sheets

(51) Int. Cl.
  *A63B 21/055* (2006.01)
  *A63B 21/16* (2006.01)
  *A63B 23/035* (2006.01)
  *A63B 23/12* (2006.01)
  *A61N 5/06* (2006.01)
  *A63B 21/00* (2006.01)

(52) U.S. Cl.
  CPC ........... *A63B 21/4043* (2015.10); *A63B 23/12* (2013.01); *A63B 2213/002* (2013.01)

(56) References Cited

U.S. PATENT DOCUMENTS

| | | | | |
|---|---|---|---|---|
| 6,258,011 | B1* | 7/2001 | Wolfe | A63B 21/16 482/117 |
| 6,908,418 | B2* | 6/2005 | Saure | 482/121 |
| 7,625,325 | B1* | 12/2009 | Yost | A63B 21/0552 482/129 |
| 2006/0183609 | A1* | 8/2006 | Flynn | A63B 21/0004 482/124 |
| 2007/0294819 | A1* | 12/2007 | Levesque | 4/524 |
| 2010/0017953 | A1* | 1/2010 | O'Keeffe et al. | 4/524 |
| 2011/0209417 | A1* | 9/2011 | Ma et al. | 52/79.1 |
| 2011/0315672 | A1* | 12/2011 | Benda et al. | 219/385 |

\* cited by examiner

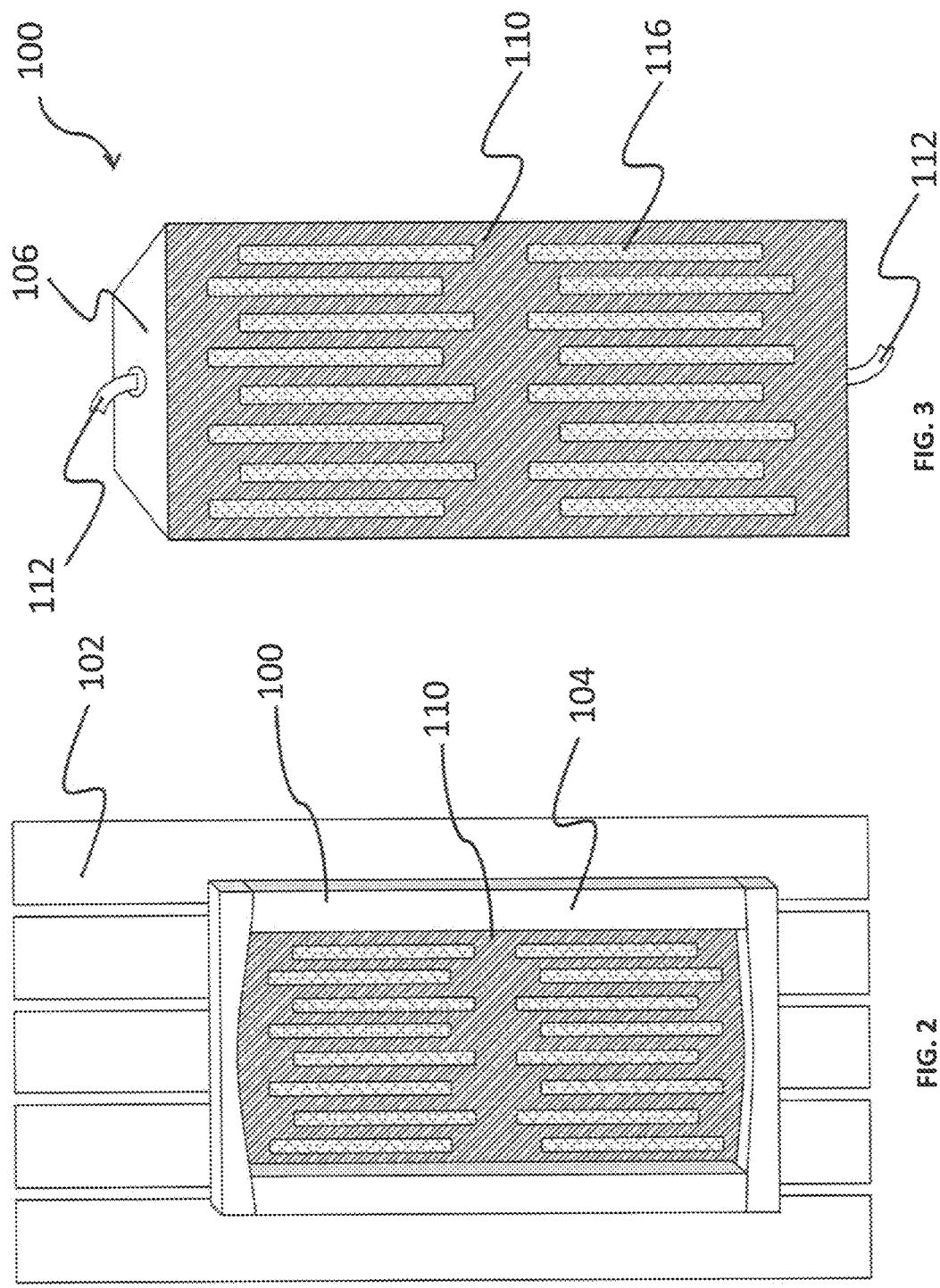

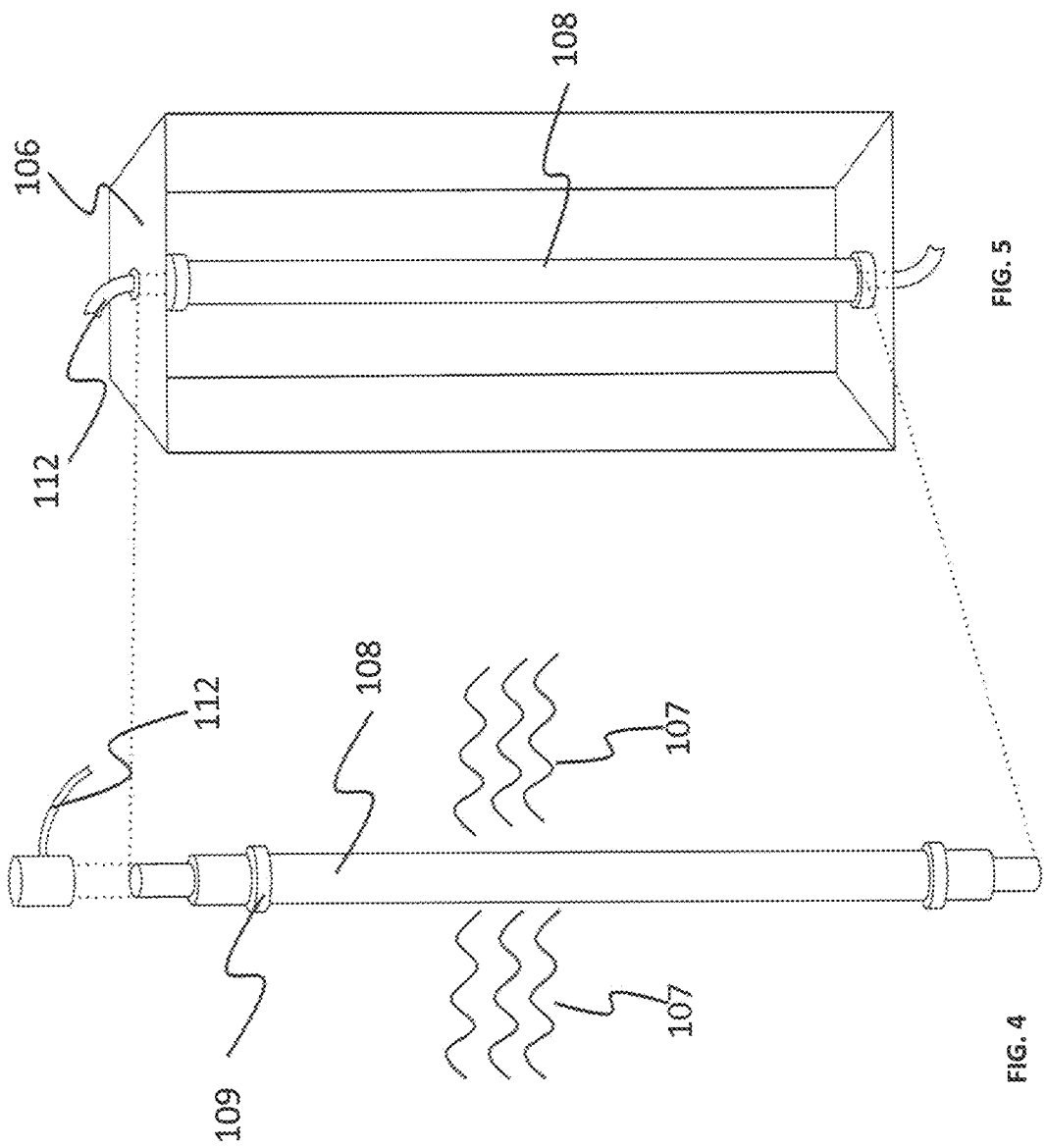

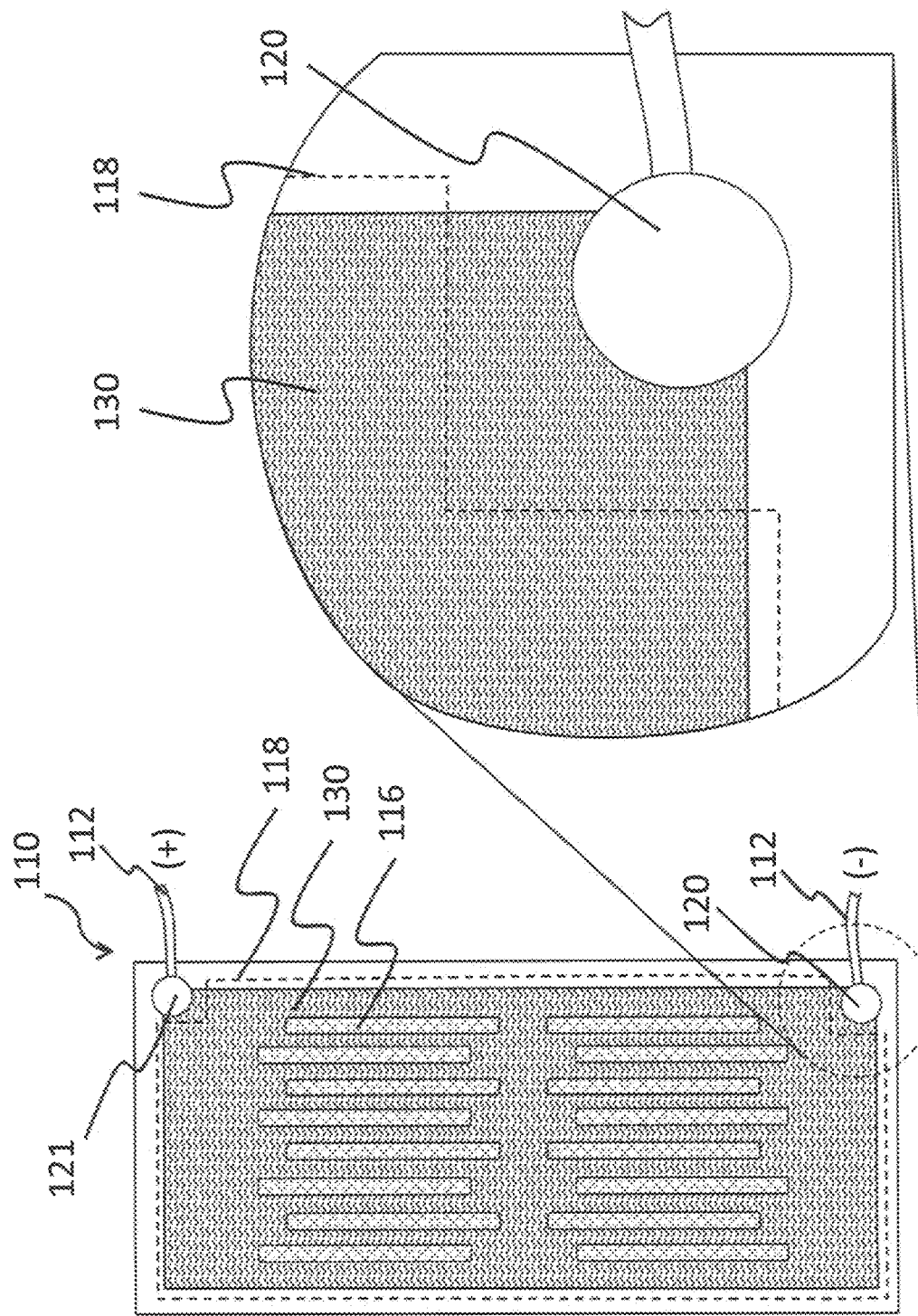

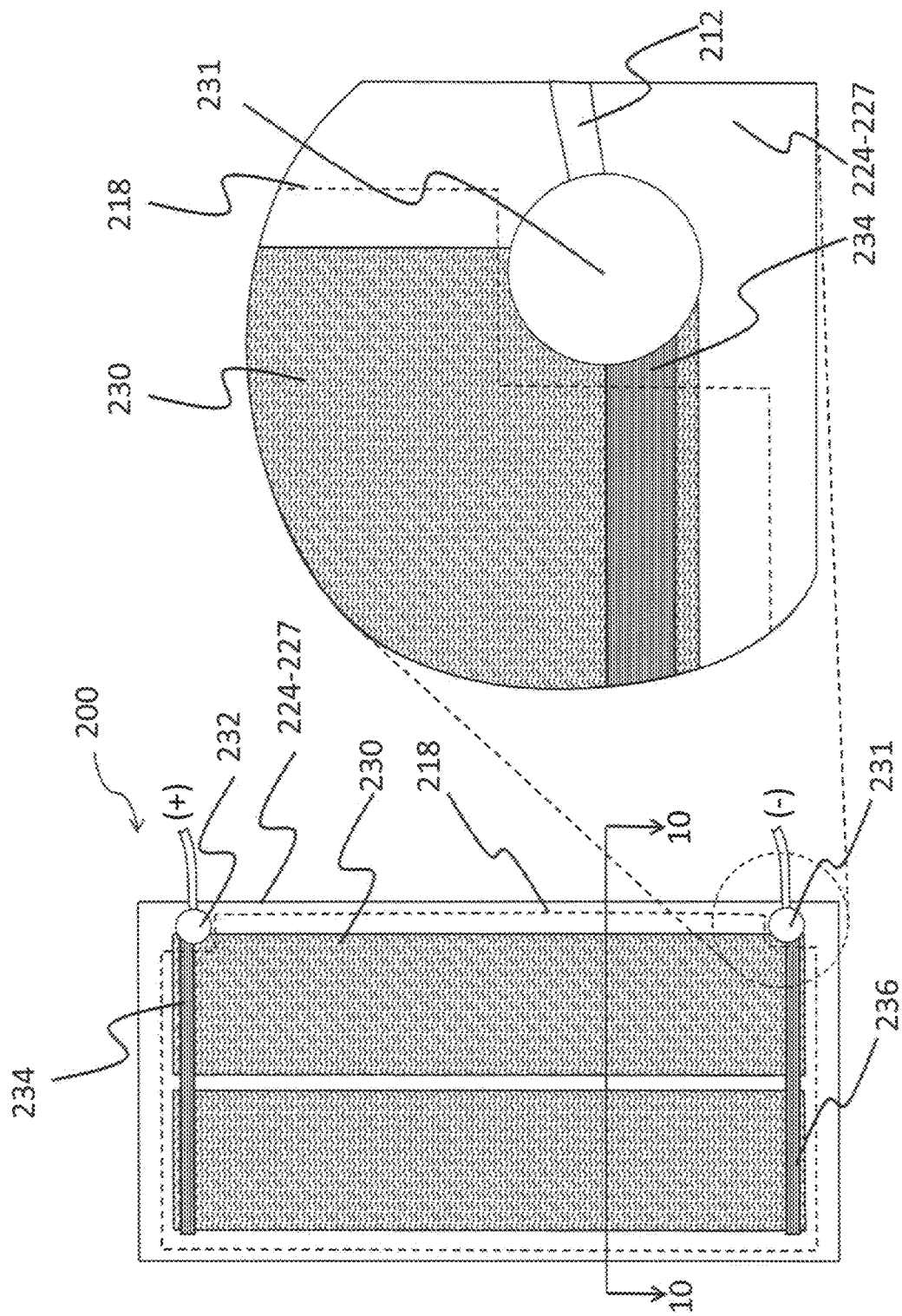

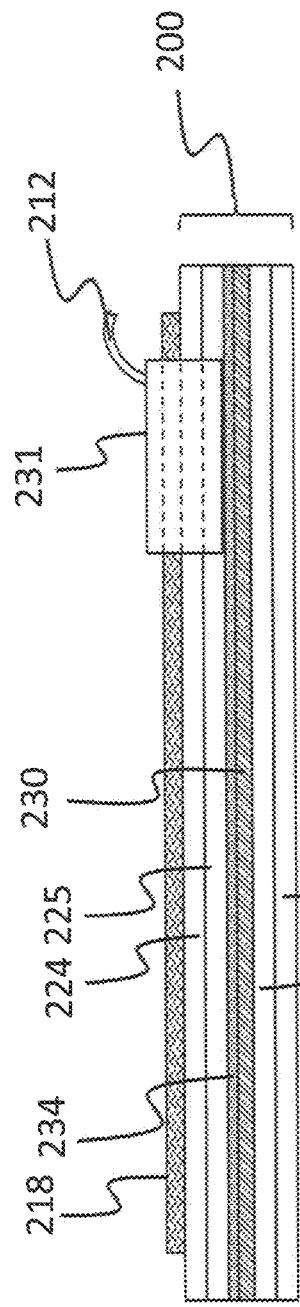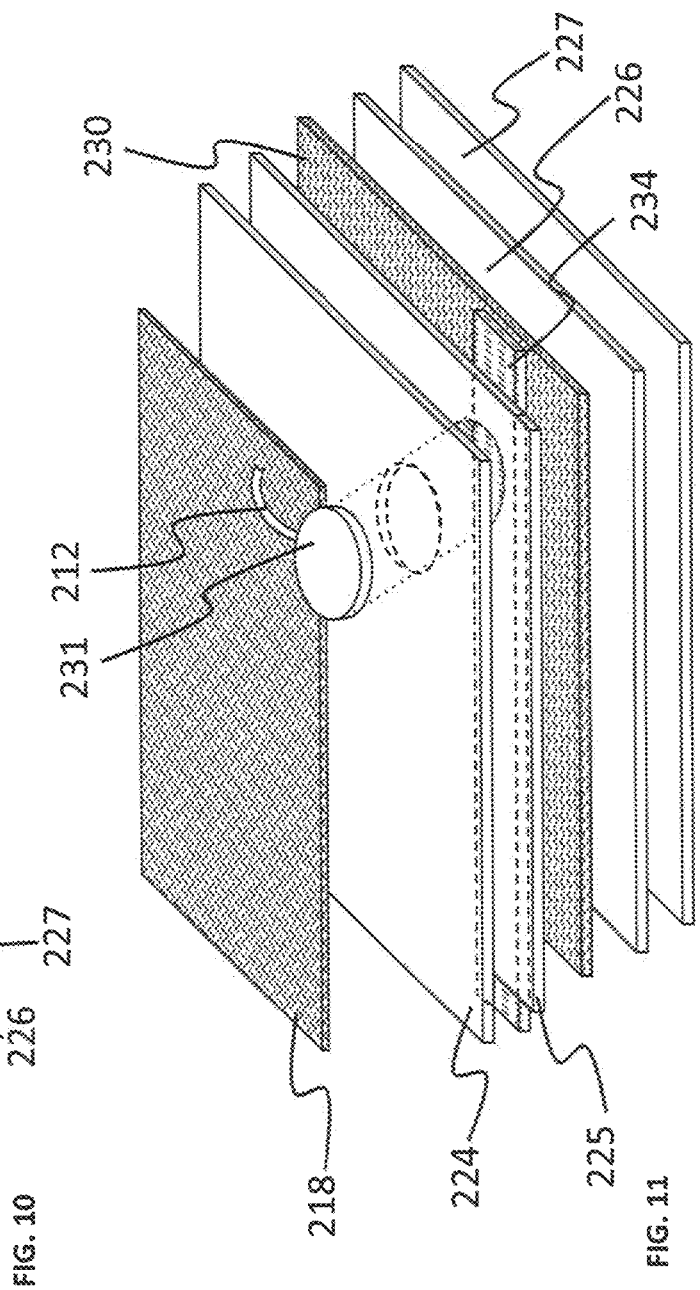
FIG. 10
FIG. 11

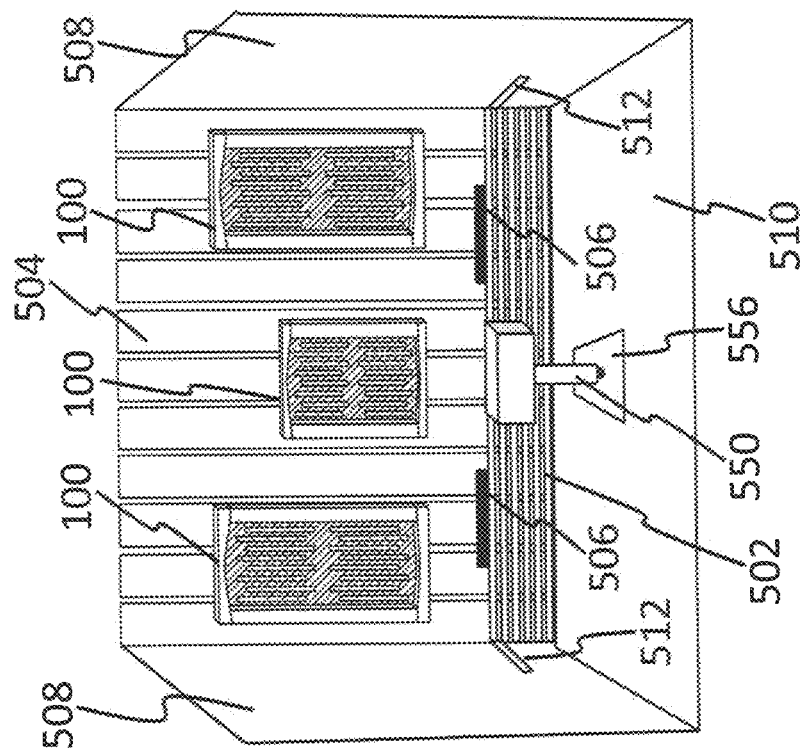
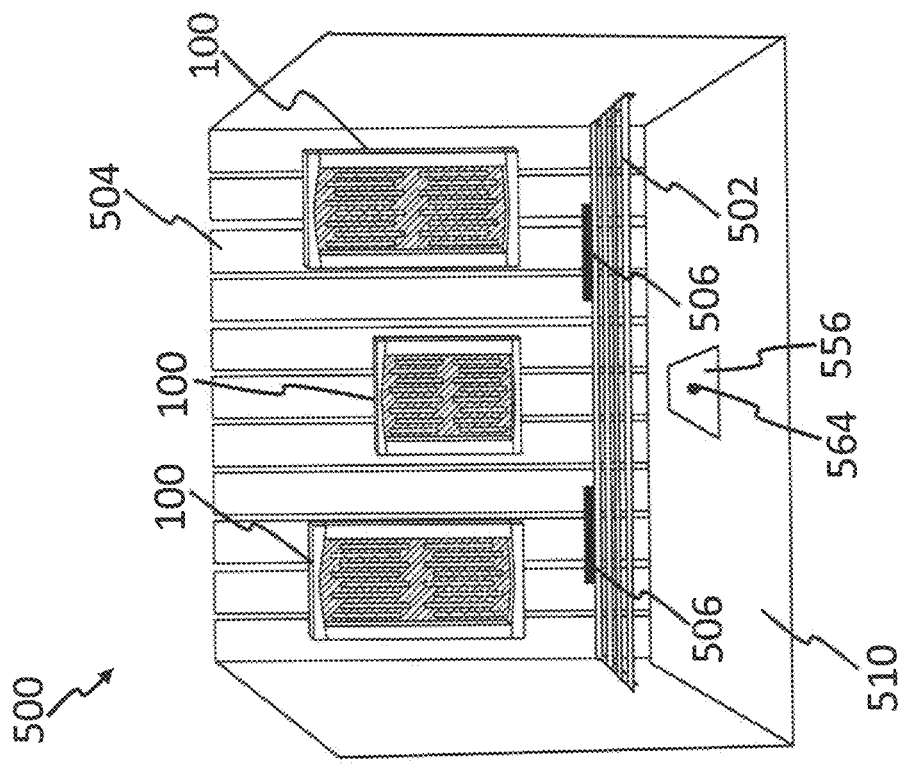

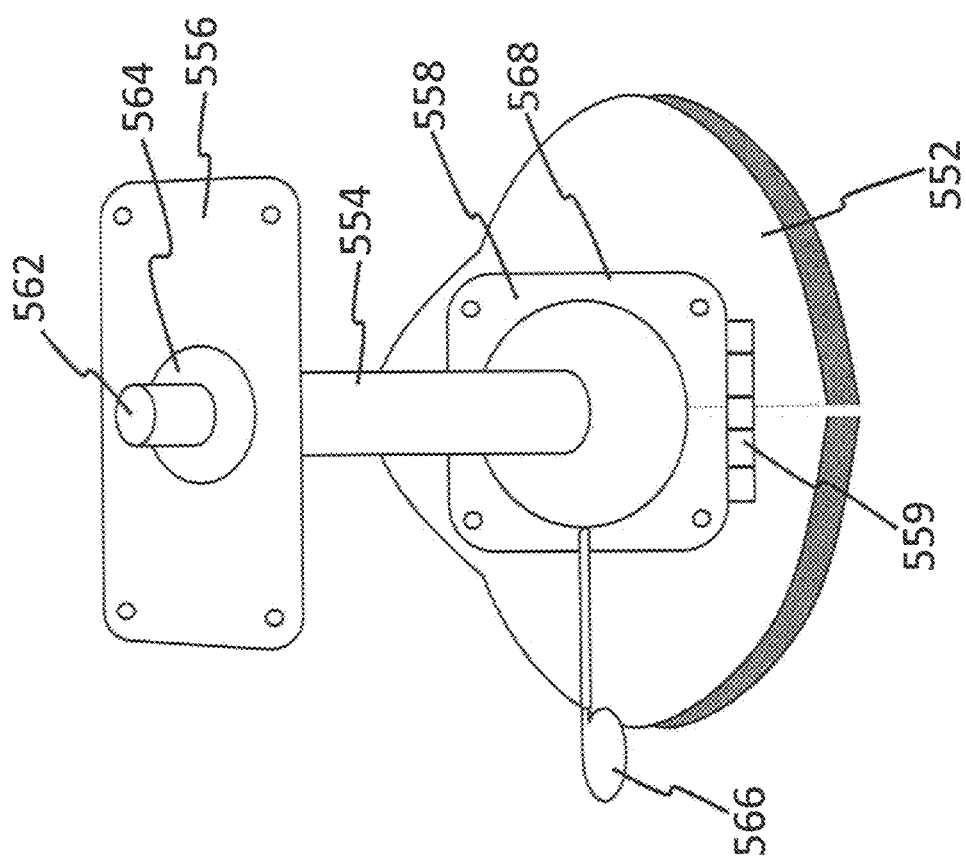

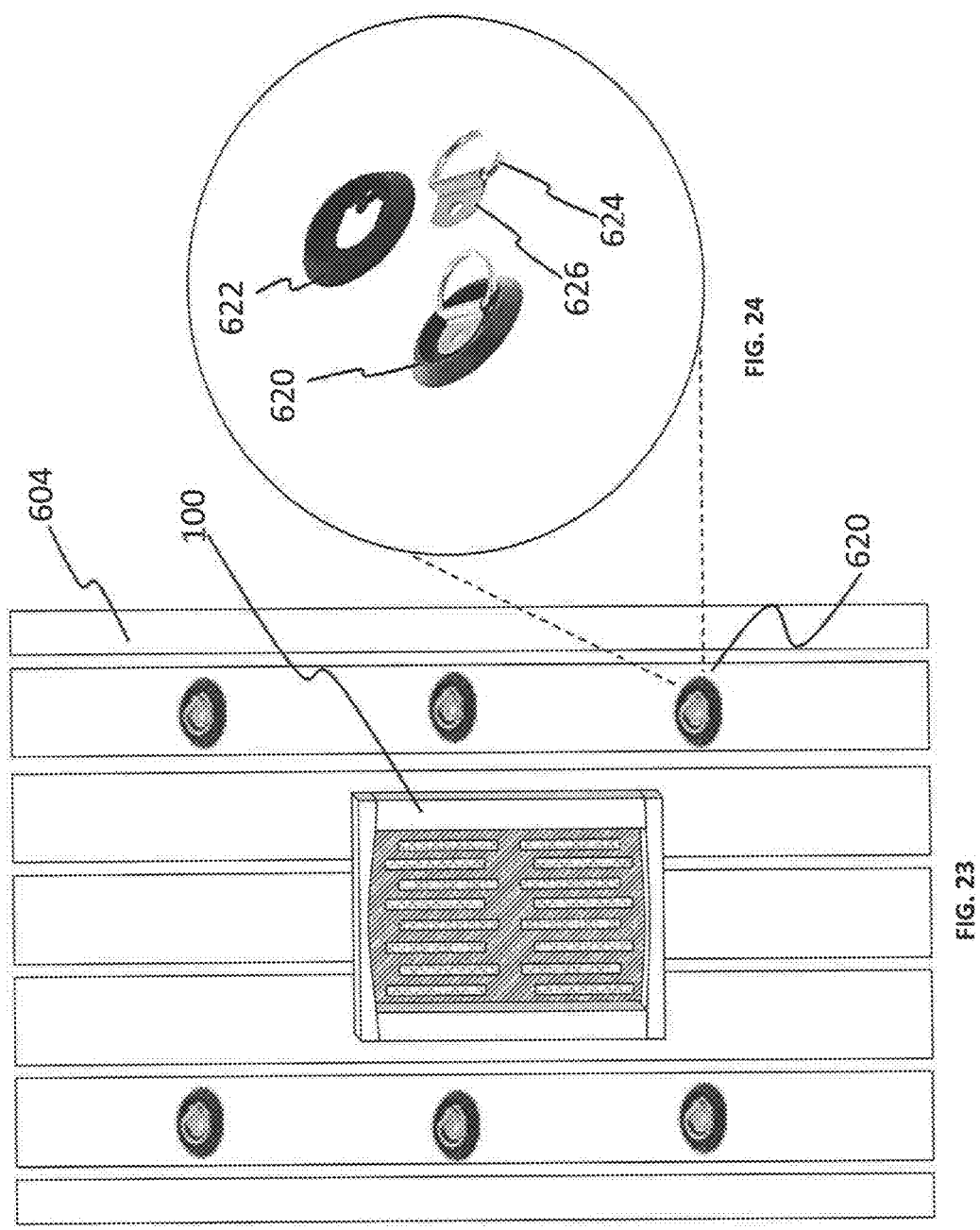

EXERCISE SAUNA HAVING FAR INFRARED HEATING ELEMENTS AND CONFIGURABLE SEATING

RELATED APPLICATIONS

This application claims the benefit of priority to U.S. Provisional Patent Application Ser. No. 61/666,839 entitled "FAR INFRARED SAUNA HAVING A PORTABLE SEATING DEVICE, A HEATED LED PANEL, AND AN EXERCISE SYSTEM", filed Jun. 30, 2012, and U.S. Provisional Patent Application Ser. No. 61/804,284 entitled "SAUNA HAVING A FAR INFRARED HEATING ELEMENTS, A HEATED PANEL, PORTABLE SEATING DEVICE, AND AN EXERCISE SYSTEM", filed Mar. 22, 2013.

BACKGROUND OF THE INVENTION

Sauna heater technology has advanced far beyond the old-fashioned hot rock era. The health benefits of saunas have been recognized for centuries, beginning with ancient Roman baths, to sweat lodges, and other primitive systems that evolved into the well-known traditional hot rock saunas and have culminated in the far infrared ("FIR") saunas one finds in the market today. All are based on the idea that heating the body and producing perspiration cleanses the cells and pores by removing unwanted substances, such as toxins and acids in the process. Typically, a heat source using wood, electric, or gas is used to produce the heat in a sauna. The old-fashioned hot rock saunas require extreme, and often, unsafe heat, which warms the room, the walls, and the entire sauna environment prior to transferring any significant heat to the individual seated within the sauna. In addition, once constructed in place, traditional electric heating elements in hot rock saunas have considerable power requirements and are often nearly impossible to move to a different location.

Thus, in recent years, far infrared technology has been used to replace the traditional hot rock saunas. Infrared ("IR") energy, or radiant heat, is commonly regarded as that electromagnetic energy with a wavelength between 0.75-1,000 microns ("μm") on the electromagnetic spectrum, bordering on the visible light spectrum. Far infrared light is usually regarded as being found in the range of wavelengths from 5.6-1000 μm, the longer wavelengths of the IR spectrum while "near" IR and "mid" IR fall in the realm of wavelengths shorter than 5.6 μm, and "nearer" the visible light spectrum with respect to frequency and wavelength. The terms "near," "mid," and "far" as applied to IR energy, all refer to their proximity to the visible light spectrum. All infrared light falls outside the visible spectrum, thus is not visible to the human eye. IR energy, or IR radiation as it is often known, including FIR, is perceptible as heat, like the warming rays of the sun. Infrared saunas use this infrared radiation, to heat the body directly, rather than heating the air, and the entire environment around the body, such as a hot rock sauna does.

IR energy, and more specifically, far infrared rays, unlike UV radiation, x-rays, or atomic radiation, are safe and often beneficial. When FIR energy hits the skin it transfers heat energy, which penetrates more than an inch and a half into the body to heal and stimulate tissues, making FIR an effective therapeutic tool for arthritis and tissue injuries among other ailments and conditions. In addition, this heating causes the individual to sweat, thus achieving health benefits similar to those from a traditional rock sauna heating techniques.

Studies indicate that the use of a far infrared sauna using the correct frequency of infrared rays triggers a process called "resonant absorption" wherein toxins are removed from the cells in our bodies at a higher rate than achieved by high ambient temperatures alone. When comparing far infrared saunas to traditional hot rock saunas, FIR has several other advantages as well. One of the most important differences between traditional hot rock saunas and FIR saunas is the infrared energy enables the IR heating elements to function at a lower surface temperature. Traditional hot rock saunas typically operate at temperatures ranging from 180° F. to 190° F. This high heat can be uncomfortable or even dangerous for some people, especially those with cardiovascular or respiratory problems and can limit the time one can spend in the sauna. This, in turn, limits the amount of sweat that can be produced due to an individual's tolerance of the environment, reducing the amount of therapy obtainable. The heavy, thick air can be difficult to breathe and evaporation can dry out membranes in the nose and eyes, furthering discomfort.

A FIR sauna, on the other hand, typically functions between 100° F. and 140° F., wherein it is estimated that less than 20 percent of the infrared energy generated by the heater goes into the air. Thus, not only does the body receive the other 80 percent of the heat directly, including all of its benefits, many individuals find that the air is more breathable, and apart from the FIR heating elements, there are no hot surfaces.

A further benefit of FIR saunas is that an infrared sauna heater uses considerably less electricity than traditional hot rock saunas that use electricity as the power source. The infrared sauna is usually ready to use within 15 to 30 minutes, whereas a traditional rock sauna (depending on their size) can take over an hour to reach optimum temperature. Moreover, many infrared saunas come in kit form and are easier to assemble, so they can be moved to a new location with relative ease, in contrast to the larger and more complicated hot rock saunas.

A central principle to the infrared sauna technology is emissivity. Emissivity is a dimensionless measurement of the relative ability of an object's surface to emit energy by radiation. Typically, the duller and darker an object, the greater its emissivity becomes. Emissivity can have a value from zero (0), as in the case of a shiny mirror that absorbs and radiates no energy, to 1.0, a theoretical maximum, described by a perfect "black body" in thermal equilibrium. The theory states a black body emits as much or more energy at every frequency than any other body at the same temperature. Real materials actually emit energy at a fraction of that of a black body; that is, real materials have emissivity values of less than 1.0. Some ceramics however, have exceptional emissivity values as high as 0.95.

Emissivity is further implicated by the way the human body radiates and absorbs heat energy, and thus IR/FIR energy. The average human body radiates and absorbs infrared energy through the skin at wavelengths of 3-50 μm with a concentration of that energy output at 9.4 μm. The goal of FIR heaters is to closely match the wavelength, and thus emissivity, thereby maximizing the rate at which the human body absorbs the IR/FIR energy, or heat. This results in more efficient, faster, and deeper absorption of radiated energy by the human body. In order to achieve this end, the heaters must be carefully designed to produce sufficient amounts of FIR energy within the appropriate band of wavelengths and frequencies.

Currently, the three (3) most common materials used in infrared heaters are ceramic, carbon, and infrared light-emitting diodes (LED). Ceramic is a very efficient and effective material when heated to produce infrared energy. Ceramic has a very high emissivity rating, thus it emits, or produces significant infrared heat. The drawback to ceramic heaters is that they tend to produce a shorter wavelength infrared energy than optimum for an FIR sauna application. This is troublesome because the human body does not as easily absorb shorter infrared wavelengths as it does longer FIR wavelengths. This renders sauna heaters that use only ceramic heating elements (and thus shorter wavelengths) less therapeutic.

In contrast, carbon infrared heaters produce a longer infrared wavelength. Carbon is very lightweight so the heaters can be bigger and can operate at a lower surface temperature. The lower surface temperatures of carbon heating elements produce longer wave infrared energy, resulting in radiated heat in the FIR spectrum. This heat is more readily absorbed by the human body and will produce results that are more desirable. The drawback of carbon heaters is that while they produce high quality FIR heat in the desired wavelength range, they do not commonly produce a significant amount of the energy, placing them lower on the emissivity curve than a ceramic heater alone.

The IR sauna market currently has a number of carbon-ceramic heaters available, however, the majority of these heaters emit the majority of their FIR energy between 0-7 µm, below the optimum, and 9.4 µm FIR energy the human body most efficiently absorbs.

Finally, LEDs provide still another option that has proven effective for IR energy production. While the wavelengths of IR energy emitted by IR LEDs are different from carbon and ceramic, their light weight and power output make them a viable alternative and useful as a heating FIR element. While an individual LED provides limited FIR output, many LEDs may be combined to form an array, creating a panel with similar characteristics to the carbon and ceramic panels discussed above. They may be further formed into smaller, portable or customizable sizes with the option of flexible mounting options for use in conjunction with, or independently from, the fixed carbon-ceramic heating elements.

Many people seeking the therapeutic benefits of infrared therapy can pay up to thousands of dollars per year for access to FIR saunas in health clubs, paying by session in spas around the country. The present invention will allow users to receive the benefit of both FIR sauna therapy and the LED therapy in the privacy of their own home.

The present invention incorporates multiple carbon and ceramic infrared panels mounted to or within the walls of the sauna cabin, in addition to one or more smaller IR LED arrays positioned to optimally transfer FIR energy to the individual sitting within the sauna. The walls and ceiling of the sauna cabin may all include such FIR-emitting panels.

A further limitation of typical saunas is interior space. Within the typical sauna, the interior is commonly outfitted with bench-style seating, allowing the user to comfortably enjoy the benefits of the sauna. The benches are most often constructed of wood, with wood slatted seats, allowing more air circulation between the seated user and the bench. Some larger saunas have multiple tiers of bench seating, allowing the user to take advantage of higher temperatures toward the ceiling and increasing available seating for multiple users. However smaller, personal saunas intended for home use are designed with efficient use of space as a primary concern, so as to minimize the sauna footprint, leaving minimal excess interior space. Moreover, while there is some flexibility in the user's physical position on the bench while seated, benches are fixed in place, restricting the user's seating options, further limiting floor space. This also leaves room for little more than simply sitting in place and sweating, as opposed to maximizing time spent with exercise or stretching.

Saunas have traditionally been used as a form of relaxation and detoxification. With the lower operating temperatures of an FIR sauna, users are now able to remain inside the sauna for up to or even exceeding one hour in duration. For most, this is a long period of time that might be used in more productive ways, such as an exercise routine. Initiating an exercise program inside a FIR heated sauna stimulates more intense workouts while stimulating even more sweat production. There is clinical evidence that conducting a resistance or anaerobic training session in such an environment is more effective for injury prevention, tissue repair, and recovery than the same workout in a normal gym environment.

Thus, by incorporating features into the construction of the FIR sauna cabin that allow the user to engage in physical exercise within the sauna cabin, a user benefits from the extended time spent in the sauna, in addition to the ability to use the time for other activities.

In light of the above, it would be advantageous to provide a far infrared heating element for IR saunas that produces the long wave infrared heat of carbon heaters combined with the very high infrared output of ceramic heaters, and the flexibility of LED-based infrared heaters. It would be further advantageous to provide a new technology that uses a combination of carbon, ceramic, and IR LEDs that can produce far infrared heat energy with a majority of that heat of a wavelength at or near the level of the human body's optimum absorption. It would further be advantageous to provide a sauna with user-configurable interior seating options and workout configurations allowing the user to exercise while simultaneously reaping the benefits of FIR therapy.

SUMMARY OF THE INVENTION

The present invention contemplates a FIR sauna, and FIR heating element that have been shown to provide a 362% faster heat up (to 120 degrees effective temperature), 462% faster sweating by the user, and 339% more sweat than a conventional sauna. An individual's use of this system results in improved detoxification of the body, cardio-respiratory benefits, accelerated weight loss, skin rejuvenation, and stress relief, all with anti-aging effects. The FIR sauna of the present invention will work for anyone, regardless of fitness level. The FIR heating element of the present invention makes optimum use of a combination of the high volume of infrared heat energy of a ceramic heating element, longer wavelength IR emissivity characteristics of carbon fiber, and the adaptable nature and flexibility of LEDs. The present invention further incorporates a flexible seating system. Additionally, the present invention has attachment points within the structure of the sauna cabin, such as integral "D" rings, allowing the user to attach exercise bands or machines and to conduct an exercise routine while seated within the sauna.

The carbon and ceramic FIR heating element of the present invention incorporates a carbon fiber panel in conjunction with an aluminum backing, and highly emissive ceramic heating element, providing a heat source that emits FIR energy with a wavelength of 7-12 µm.

The wavelength of the IR energy created by the carbon and ceramic heating element of the present invention is significant due to the absorption characteristics of the human body. The average human body radiates and absorbs infrared energy through the skin at 3-50 µm with a concentration of that energy output at 9.4 µm. The heating element of the present invention emits FIR energy with the majority of radiated heat output in the FIR band, from 7-14 µm, the output spread evenly around the 9.4 µm pivot point of peak human output. This results in more efficient, faster, and deeper absorption of radiated energy by the human body. This distribution maximizes the higher degree of penetration by the FIR waves that produce resonant absorption within human tissue, melting subcutaneous fatty deposits and releasing the toxins stored therein.

The deeper penetration and more efficient absorption of the FIR energy and heat by the human body produces a much heavier sweat than hot rocks saunas, steam saunas, and exercise. FIR saunas expose the human body to enough directed FIR energy to melt fat and draw out toxins stored subcutaneously. The toxins are then carried out of the body as the body sweats, purifying the body.

The benefits of using the hybrid carbon-ceramic heating system of the present invention are not limited to the emitted IR energy. The low weight—typically less than one (1) pound—of the carbon panel, and other components such as the ceramic heating element, and surrounding aluminum construction provide the user with a lightweight, versatile solution to an infrared sauna heater. This characteristic allows FIR heaters to have larger surface areas, further allowing them to operate at lower surface temperatures maximizing FIR output and making them significantly simpler to construct and easier to transport than traditional hot rock sauna heaters. If constructed from stainless steel, the shroud becomes slightly heavier, but because stainless steel is more IR-reflective than aluminum, less IR energy is lost.

IR LEDs also provide a source for FIR energy that may be employed in conjunction with the carbon and ceramic heating elements. The present invention employs additional IR LED arrays arranged on panels installed within the sauna on flexible or movable mounts. This feature allows the user to move the panel and direct it at a specific area of the body, such as the face or calf, depending on the user's needs. This allows a user to experience FIR heat from the LED panel directly on their face, or other body part, while simultaneously benefiting from the deep penetrating far infrared energy produced by other heating elements within the sauna itself. This double benefit is significant to users.

A further advantage of the present invention is encompassed in the seating options provided. While standard bench seats limit space available within the sauna cabin, the present invention facilitates a solution to this lack of versatility and increases the user's comfort, by providing more versatile seating solutions. Instead of being limited to a fixed bench seat, the present invention includes a hinged bench seat, allowing the user to lift the seat by way of hinges, fold the bench seat into a vertical position, and attach the folded seat to the back wall inside the sauna. The hinged seat not only allows the user to move the bench seat out of the way, increasing floor space within the sauna, but also allows access to a single, pedestal-style seat that may be stored beneath the bench seat while the bench is in the down position. The single, pedestal-style seat may further be affixed to the floor of the sauna giving the user additional seating options and facilitating the conduct of an exercise routine using the sauna's integral "D" rings, discussed below. The seating options further provide freedom of movement and convenience for the user when the seat is in use, and easily stores underneath the fold down bench, out of site, when not in use.

Still another advantage of the present invention is the plurality of "D" rings" or other similar devices installed within the interior of the sauna allowing the user to exercise while using the FIR sauna. These "D" rings can be used as attachment points for exercise implements such as elastic bands or even small workout machines, while the additional space provided enables a user to move about, stretch, perform exercises, and enjoy more freedom of movement within the confines of a FIR sauna, all while simultaneously benefiting from the deep penetrating FIR heat.

To facilitate the incorporation of the "D" rings into the structural design of the sauna cabin and provide a stable and secure mounting point, the walls of the cabin also incorporate an external curvature or arch-shape increasing the structural strength of the cabin. The external curvature provides additional strength by distributing force across the wall, and away from the center of force on the "D" ring, (much like the support provided by an arch) counteracting opposing forces imparted on the interior of the cabin when an individual makes use of the "D" rings during exercise.

BRIEF DESCRIPTION OF THE DRAWINGS

The nature, objects, and advantages of the present invention will become more apparent to those skilled in the art after considering the following detailed description in connection with the accompanying drawings, in which like reference numerals designate like parts throughout, and wherein:

FIG. 2 is a front plan view of the far infrared heating element of the present invention as installed in a wall of an IR sauna cabin, depicting the slotted front of the carbon panel, and enclosure built around the face of the far infrared heating element;

FIG. 3 is a perspective view of the front of the far infrared heating element of the present invention depicting the carbon panel, slotted openings in the carbon panel, shrouded metal enclosure, and power supply cords;

FIG. 4 is a front view of the ceramic heating element prior to installation in the FIR heating element of the present invention, depicting the power cords and mounting surfaces;

FIG. 5 is a front view of the FIR heating element of the present invention with the carbon panel removed, depicting the ceramic heating element, and its position within the metal shroud and power supply cords for the ceramic heating element;

FIG. 6 is the back view of the carbon panel, as removed from the FIR heating element of the present invention, depicting the position of the heating layer, the backing on the carbon panel, heating layer, the associated slots in the carbon panel, and the electrical connections thereon;

FIG. 7 is a close up view of one of the electrical connections on back of the carbon panel of the present invention depicting the backing, the heating layer, and the cutout in the aluminum backing that accommodates the electrical connection to the back of the carbon panel;

FIG. 8 is the back view of an alternate embodiment of the carbon panel without slotted openings, as removed from the FIR heating element of the present invention, depicting the backing (in dashed lines), the position of the electrical connections, and the electrical current bus that distributes current to the carbon heating layers;

FIG. 9 is a close up view of one of the electrical connections on the back of the alternate embodiment of the carbon panel of FIG. 8, depicting the backing, electrical current bus, and the cutout in the backing that accommodates the electrical connection to the back of the current bus and carbon panel;

FIG. 10 is a cross section of the carbon panel, showing the insulation layers on both sides of the carbon panel, the heating layer, the electrical current bus, and the aluminum backing;

FIG. 11 is an exploded perspective view of the various layers of the carbon panel of FIG. 8, showing the interaction of the two insulation layers on both sides of the heating layer, the electrical connection to the current bus, and the backing;

FIG. 15 is a cut away of the inside of a sauna cabin, showing a FIR heating element installed on the back wall, a bench seat attached with hinges to an adjacent wall, and the seat base plate of the pedestal seat assembly installed in the floor of the sauna cabin;

FIG. 16 shows the inside of a sauna cabin, depicting the bench seat stowed against the wall allowing installation of the pedestal seat assembly in the seat base plate in the sauna floor;

FIG. 19 is a rear bottom view of the pedestal seat showing the base plate, seat pole, hinge assembly, height control lever, and seat;

FIG. 23 is a plan view of the front of the FIR heating element of the present invention depicting the "D" rings where exercise bands would clip or snap on;

FIG. 24 is an exploded view of a preferred embodiment of the "D" ring assembly, showing the mounting hardware, "D" ring, and protective grommet;

DETAILED DESCRIPTION

Figure 1:
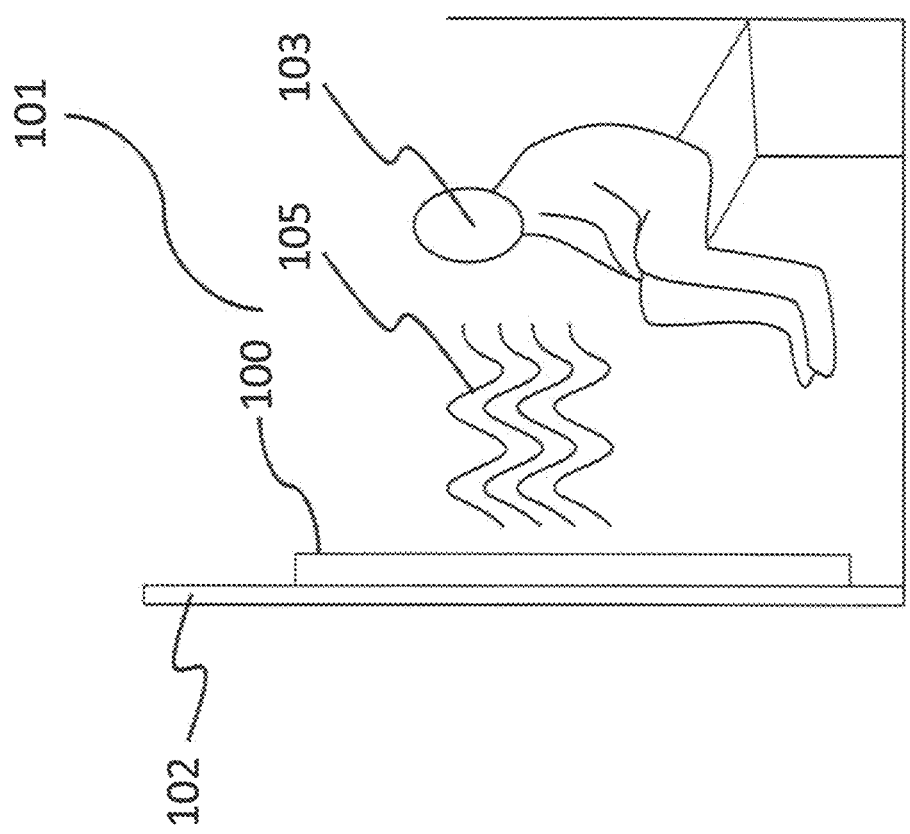
FIG. 1 is a side, cut away view of the interior of an infrared (IR) sauna cabin, with an individual seated therein, and facing the far infrared heating element of the present invention as installed in a wall of the IR sauna cabin, and absorbing the FIR energy emitted by the far infrared heating element.

Referring initially to FIG. 1, a cut away view of an exemplary IR sauna cabin, generally labeled 101, is depicted showing an individual 103 seated therein. The far infrared ("FIR") heating element of the present invention, generally labeled 100, is shown installed in wall 102 of sauna cabin 101. The FIR heating element 100 is shown radiating combined FIR energy 105 in order to heat the individual 103 and cause individual 103 to sweat, providing therapeutic benefits, such as resonant absorption of the FIR energy 105 within individual's 103 bodily tissues.

Referring now to FIG. 2, FIR heating element 100 is depicted, installed in a sauna wall 102. The FIR heating element 100 of the present invention is contemplated herein as a sauna heater, thus it is shown installed in a wooden enclosure 104, however it should be appreciated by those skilled in the art, that the FIR heating element 100 may be used for other purposes or installed in a variety of other enclosures, such as metal or composite materials.

Referring now to FIG. 3, the FIR heating element 100 is shown prior to installation in a sauna. A metal shroud 106 provides structural support and mounting points for the ceramic heating element 108 (shown in FIG. 4) and carbon panel 110. Metal shroud 106 further provides mounting points to allow the entire FIR heating element 100 to be mounted in place or on the sauna wall 102 (shown if FIG. 2). Electrical cables 112 provide electrical power to FIR heating element 100, and more specifically electrical power individually to ceramic heating element 108 and carbon panel 110. The power applied is distributed to the carbon panel 110 either directly (described in conjunction with FIGS. 6 and 7), or by use of an electrical current bus (described in conjunction with FIGS. 8 and 9).

It is to be appreciated by those skilled in the art that metal shroud 106 may be constructed from various metallic or other IR-reflective materials known in the art. A purpose of metal shroud 106 is to reflect IR energy in the direction of individual 103. Various types of steel, aluminum, or alloys are suitable for this type of application. Metal shroud 106 may also take many different shapes and sizes, varying the reflective properties and direction of reflected energy.

FIG. 3 depicts a plurality of slots 116 formed within the carbon panel 110. This Figure shows 16 slots 116 for illustrative purposes. The number of slots may vary with the size of carbon panel 110, desired output of the FIR heating element 100, and application thereof. In other words, the number of slots 116 depicted should not be viewed by those skilled in the art as a limiting characteristic of the present invention. More specifically, slots 116 are implemented to allow a greater volume of the IR energy produced by the ceramic heating element 108 to flow through the carbon panel 110 in order to reach the individual 103 inside the sauna cabin 101. The number of slots 116 described herein is therefore fully adaptable to create a specific IR energy output while maximizing the desired FIR energy 105 output.

Referring now to FIG. 4, the ceramic heating element 108 is depicted, as it would be found prior to installation in FIR heating element 100. The ceramic heating element 108 used in the construction of FIR heating element 100 may be one of the many varieties of ceramic heating elements commercially available in the market. This Figure shows the cylindrical nature of the ceramic heating element 108, in addition to its mounting points 109. When power is applied via electrical supply 112 across the ceramic heating element 108, the impedance of ceramic heating element 108 causes a transfer of energy resulting in ceramic heating element 108 heating up. As ceramic heating element 108 increases in temperature, it begins radiating IR energy. This radiation flows radially away from ceramic heating element through slots 116 in carbon panel 110 to the individual 103 inside the sauna cabin 101. IR energy 107 flowing toward metal shroud 106 is reflected, so this energy also flows through slots 116. The IR energy emitted by ceramic heating element 108 combines with FIR energy 105 emitted by carbon panel 110 to provide individual 103 with combined FIR energy 105, as shown in FIG. 1.

Referring now to FIG. 5, ceramic heating element 108 is installed in metal shroud 106. The interior shape of metal shroud 106 is optimally designed to reflect the IR energy 107 away from the FIR heating element 100 and direct the IR energy 107 toward the individual 103 inside the sauna cabin 101. It is to be appreciated by those skilled in the art that the shape of metal shroud 106 is variable based on application. In the present embodiment, metal shroud 106 and ceramic heating element 108 are placed behind carbon panel 110 in an effort to minimize the overall size of the FIR heating element 100. As will be explained in additional embodiments, ceramic heating element 108 may be placed alongside carbon panel 110, or multiple ceramic heating elements 108 may be employed to increase the volume or modify the direction of IR energy 107 emitted.

Referring to FIG. 6, the reverse side of the carbon panel 110 is shown. This Figure depicts aluminum backing 118 (shown in dashed lines) adhered to carbon panel 110, slots 116 formed in the panel 110, electrical connections 120 and 121, and heating layer 130. The focus of this figure is electrical connections 120 and 121. Electrical cables 112 provide electrical power to the ceramic heating element 108, and to electrical connections 120 and 121. Electrical connections 120 and 121 are affixed to the back of carbon panel 110, and create an electric potential across carbon panel 110, transferring an electrical charge to the heating layer 130 within carbon panel 110 when energized. The electric potential creates an electric current through heating layer 130 of the carbon panel 110. Heating layer 130 is composed of carbon fiber. Since metals, such as aluminum, conduct more heat than carbon fiber, the aluminum backing 118 is fit in place to assist in distributing the heat across carbon panel 110. Such an arrangement more evenly distributes the heat produced by carbon panel 110 and more efficiently heats carbon panel to an appropriate temperature. Carbon panel 110 then increases to approximately 100°-140° F. and emits IR energy 107 in the desired FIR band.

As carbon panel 110 increases in temperature and begins to emit FIR energy 105, the FIR energy 105 is radiated in all directions. Aluminum backing 118 further serves to direct (and reflect) FIR energy 105 emitted by carbon panel 110 toward individual 103.

FIG. 7 is a close-up view of electrical connection 120. In a preferred embodiment, electrical connection 120 is identical to electrical connection 121, differing only in the polarity of the electrical charge. It should be appreciated by a person skilled in the art that electrical connections 120 and 121 are polarity insensitive. This Figure depicts electrical connection 120 affixed directly to heating layer 130 of carbon panel 110 and aluminum backing 118 as a dashed line. In this embodiment, the electrical potential is applied directly to the carbon material within heating layer 130.

Referring to FIG. 8, an alternative embodiment of carbon panel is shown and generally designated 200. In this embodiment, heating layer 230 is constructed of pulverized carbon or carbon fiber and is the active heating element of carbon panel 200 of the present invention. Once electrified via electrical connections 231 and 232, heating layer 230 produces the FIR energy 105 desired by the present invention. In order to more efficiently distribute an electrical charge across heating layer 230, current bus 234 is implemented, providing a direct electrical connection between heating layer 230 and electrical connections 231 and 232 via the pulverized carbon or carbon fiber.

Depending on the composition of the carbon in heating layer 130, electrical connections 120, 121, such as those shown in FIGS. 6 and 7, might cause uneven heating of heating layer 130 should the conductive properties of the carbon be inadequate to conduct electricity evenly across heating layer 130. In that situation, power applied to carbon panel 110 may heat a limited area around electrical connections 120, 121 more than the rest of the entire heating layer 130. This may cause "hot spots" where electrical connections 120, 121 are made, in FIGS. 6 and 7. The hot spots can burn the carbon in that area of heating layer 130 and result in a shorter operational life for the entire carbon panel 110. To combat this, carbon panel 200 employs current buses 234 and 236 to provide longer electrical connections to heating layer 230 thereby creating a more even electrical current distribution in heating layer 230. Electrical connections 231 and 232 connect directly to current buses 236 and 234 respectively, which is in direct electrical contact with heating layer 230 and allows for more effective and efficient transmission and distribution of electrical potential across carbon panel 200, creating a more even electrical connection across the width of heating layer 230.

In an embodiment, carbon panel 200 utilizes copper current buses 234 and 236 to conduct and distribute the electrical current across heating layer 230. Copper is known in the art as a particularly conductive material commonly used in electrical wiring and readily availability in the market. This aspect however does not preclude the use of other conductive metals for current buses 234 and 236, such as aluminum. Current buses 234 and 236, on either end of heating layer 230, evenly distribute the electrical charge across both ends of heating layer 230 due to the effectively zero (0) resistance of current busses 234 and 236, and thus enhances heat distribution across carbon panel 200. This results in the effective alleviation of the hot spots that could form around electrical connections 231 and 232.

In an embodiment, such as that described by FIG. 8, carbon panel 200 has multiple, narrower heating layers 230, as shown. Due to the limited conductive properties of carbon fiber as discussed, the narrow design is appropriate in some circumstances. The narrower width of heating layers 230 in FIG. 8 reduces the distance an electrical charge must travel, further reducing the chances of hot spots in heating layers 230. The number of heating layers 230 selected herein (two) is chosen for illustrative purposes only and is not intended to be limiting. Composition of the carbon and power applied to the system, among other factors, may dictate a different width, number of heating layers 230, and their shape.

FIG. 8 further depicts the position of insulating layers 224, 225, 226, and 227. Insulating layers 224, 225, 226, and 227, more accurately depicted in FIG. 10, serve to insulate heating layer 230, electrical connections 231 and 232, and current buses 234 and 236 from lost voltage and heat, or other interference. Insulating layers 224, 225, 226, and 227 further provide structural support and rigidity for heating layer 230. In this alternative embodiment, insulating layers 224, 225, 226, and 227 are constructed from multiple layers of fiberglass and resin. These layers become translucent when cured and allow for easy transmission of FIR energy 105 when heating layer 230 is energized. Those skilled in the art will appreciate that other materials, apart from fiberglass, may be utilized for this purpose. Urethane, Plexiglas, Lucite, or other non-conductive, heat-resistant materials with similar characteristics may be employed for the same purpose. Fiberglass was chosen for the present embodiment due to its minimal weight, flexibility, and ease of construction; however, this should not be viewed as a limiting aspect of the present invention. In an embodiment, the flexible nature of the fiberglass further allows for installation of carbon panel 200 in a non-linear manner, should a design call for a curve in the shape of carbon panel 110.

Referring to FIG. 9, a close up view of the electrical connection 231, as depicted in FIG. 8, is shown. This Figure shows aluminum backing 218 in dashed lines. As installed, heating layer 230 is not visible from the back of carbon panel 200, as the aluminum backing 218 covers the majority of heating layer 230 and current buses 234 and 236.

Referring now to FIG. 10, a cross section of carbon panel 200 is shown. Electrical connection 231 (or 121 of carbon panel 110) imparts an electric potential across heating layer 230. Electrical connection 231 is shown in this Figure in direct contact with current bus 234, and is shown in dashed lines where it passes through insulating layers 224 and 225 as well as aluminum backing 218. Insulating layers 224, 225, 226, and 227 provide a barrier for the electricity imparted by the electrical potential across carbon panel 200, and more specifically heating layer 230.

Heating layer 230 and current bus 234 are sandwiched between insulating layers 224 and 225 and insulating layers 226 and 227, where an adhesive, such as epoxy resin, holds them in place. Further, aluminum backing 118 is secured to the back of carbon panel 110 with an adhesive.

In an embodiment, other suitable metallic materials are substituted for aluminum and copper in the present invention. Aluminum and copper are readily available in the market and provide suitable electrical performance for the present invention at a reasonable expense; however, other embodiments could utilize other conductive materials for current busses 234 and 236, such as nickel, gold, silver, or any one of innumerable metal alloys.

FIG. 11 depicts an exploded, perspective view of the cross section of carbon panel 200. In an embodiment, carbon panel 200 has six (6) layers: insulating layers 224, 225, 226, and 227, heating layer 230, and aluminum backing 218. Heating layer 230 is sandwiched between them, as shown in this Figure and FIG. 10. Current bus 234 is in direct electrical contact with heating layer 230 and electrical connection 231. This cross sectional view is also representative of carbon panel 110 as in FIGS. 6 and 7, except for the sole addition of current bus 234.

The six (6) layers described herein are not intended to be limiting. The thickness of insulating layers 224, 225, 226, and 227 may dictate more or fewer layers, in addition to the thickness and conductive properties of the carbon within the heating layer 230. Moreover, a different material may be substituted for aluminum backing 218 to provide the same functions.

Carbon Panel

The length of the carbon fibers that make up heating layer 130 is significant. Carbon fibers themselves are approximately 5 µm-10 µm thick and the narrow dimensions of the fibers determine the ultimate FIR energy 105 output of the entire carbon panel 200 (or carbon panel 110). As the heating layer 230 increases in temperature, due to inherent qualities and emissivity, the carbon fibers within heating layer 230 emit radiation, ideally in the FIR spectrum. The fibers themselves, as well as carbon panel 200 (and heating layers 230) may be varied in size, allowing the manufacturer to "tune" the wavelength of the FIR energy 105 and amount of energy that is radiated therefrom, in order to achieve the precise 9.4 µm desired for optimum resonant absorption by the human body.

In an embodiment, the carbon material comprising the heating layer 130 or 230 is doped with additional compounds, such as semi-conductor compounds, that may further "tune" the FIR energy 105 output. Since the surface temperature of carbon panel 200 has a direct effect on the FIR energy 105 output of FIR heating element 200, a modified carbon compound within heating layer 230 that adjusts conductivity of the carbon will directly affect the surface temperature of carbon panel 200, and thus the FIR energy 105 output of the entire system.

Figure 12:
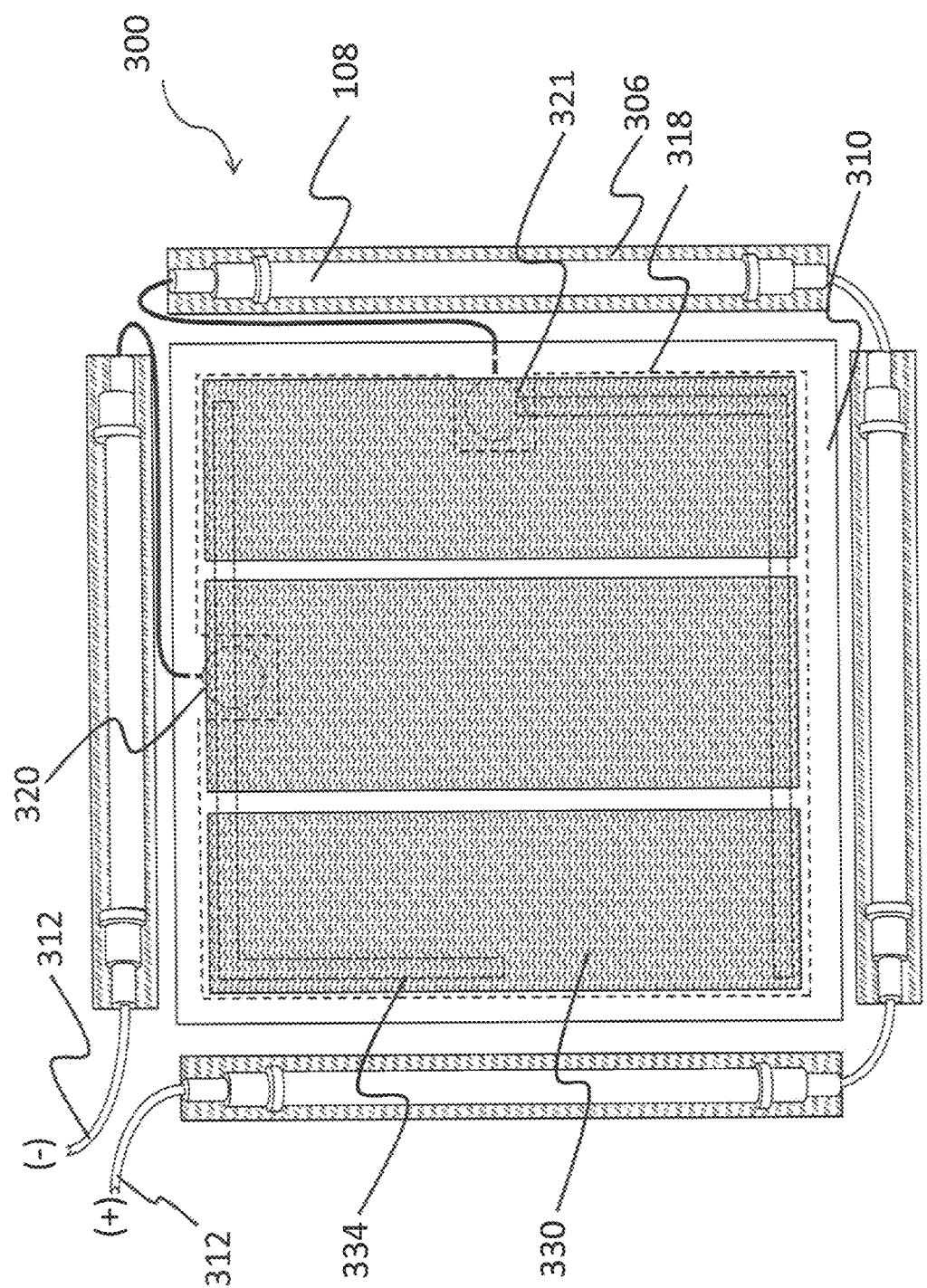
FIG. 12 is another alternate embodiment of the FIR heating element of the present invention, depicting a larger carbon panel having three heating layers, and four ceramic heating elements, spaced peripherally around the four sides of the carbon panel, with associated metal shrouds and electrical connections.

Now referring to FIG. 12, shown is another alternative embodiment of the FIR heating element of the present invention and generally referred to as 300. This embodiment includes four ceramic heating elements 108 placed along the four sides of carbon panel 310, each housed in its own metal shroud 306. Metal shrouds 306 provide similar function as metal shroud 106 above, reflecting IR energy 107 from the ceramic heating elements 108 in use, toward the individual 103 seated within IR sauna cabin 101. In this embodiment, ceramic heating elements 108 are not placed behind carbon panel 110, and therefore like the previous alternate embodiment, slots analogous to slots 116 are not required. This embodiment is designed for larger FIR heating element 300 applications within an IR sauna cabin 101.

In this alternative embodiment, the operation of FIR heating element 300 is ostensibly the same as described above. Electrical power is supplied by electrical cables 312, to power all four ceramic heating elements 108, in addition to providing electrical power to electrical connections 320 and 321 (shown in dashed lines) and current buses 334 (shown in dashed lines). Once powered, the electrical potential is present across larger carbon panel 310, transferring heat. Ceramic heating elements 108 in this alternative embodiment provide IR energy as before, with more combined surface area and approximately four times the output as a single ceramic heating element 108. In this embodiment, ceramic heaters 108 and carbon panel 310 are electrically connected in a serial configuration. It is to be appreciated by someone skilled in the art that power to ceramic heaters 108 and carbon panel 310 can be by an electrically parallel configuration, an electrically serial configuration, or a combination of parallel and serial configurations, depending on the needs of the actual sauna cabin 101 design and the power requirements of the individual components.

Larger carbon panel 310 is shown in FIG. 12 having three heating layers 330, however it is to be appreciated that like the previous alternate embodiment, larger carbon panel 310 may be formed with many different variations in the number of smaller heating layers 330 and their orientation with respect to each other and the sauna cabin 101 itself.

Located behind heating panels 330 is aluminum backing 318 (shown in dashed lines). The function of aluminum backing 318 is similar to aluminum backing 118 shown in FIGS. 6 and 7 and aluminum backing 218 in FIGS. 8-11. In this embodiment, aluminum backing does not have slots 116 as shown in FIG. 6 since there is not a ceramic heater located behind the aluminum panel 318 that would require the use of slots to allow IR energy 117 to pass through.

In an embodiment, current buses 334 may further be enlarged or lengthened to optimize the voltage and current applied to the heating layer 330.

Figure 13:
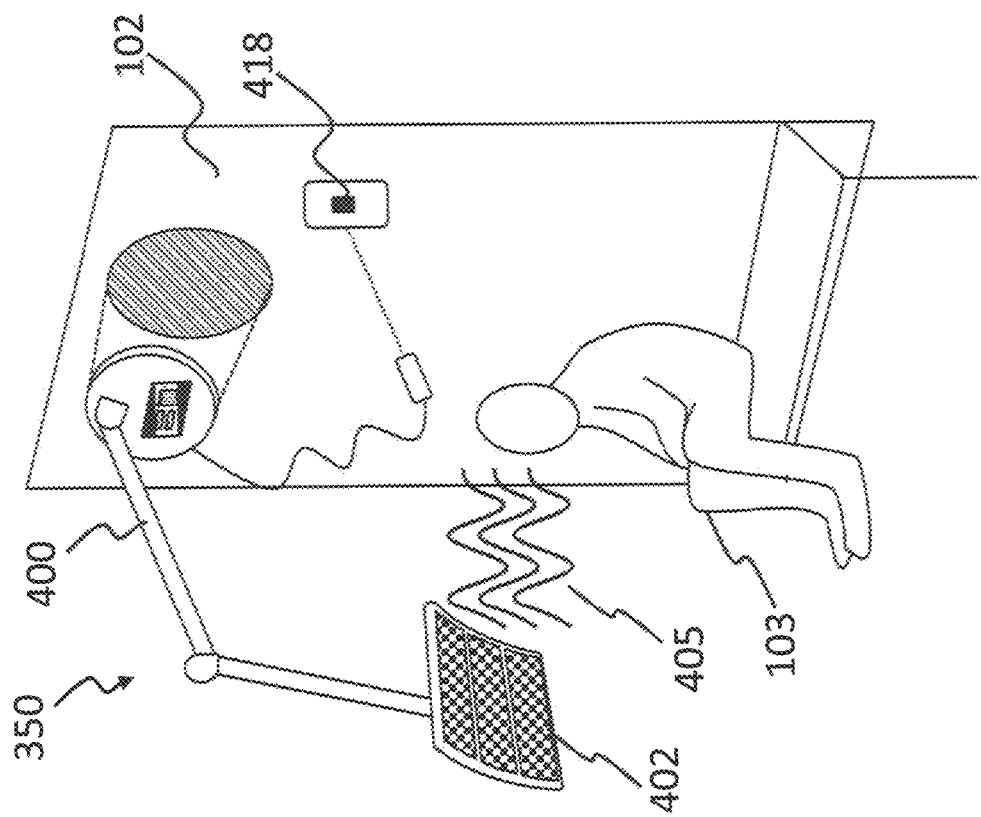
FIG. 13 is a perspective view of the back wall of a sauna cabin, to which the base plate of the LED panel assembly is attached, showing power adapter on the back wall, next to the base, LED panel extended away from the sauna wall.

Referring now to FIG. 13, user 103 is seated in the exemplary sauna cabin 101, depicted with the further addition of LED panel assembly, generally labeled 400, attached to the back wall 102 of sauna 101.

Figure 14:
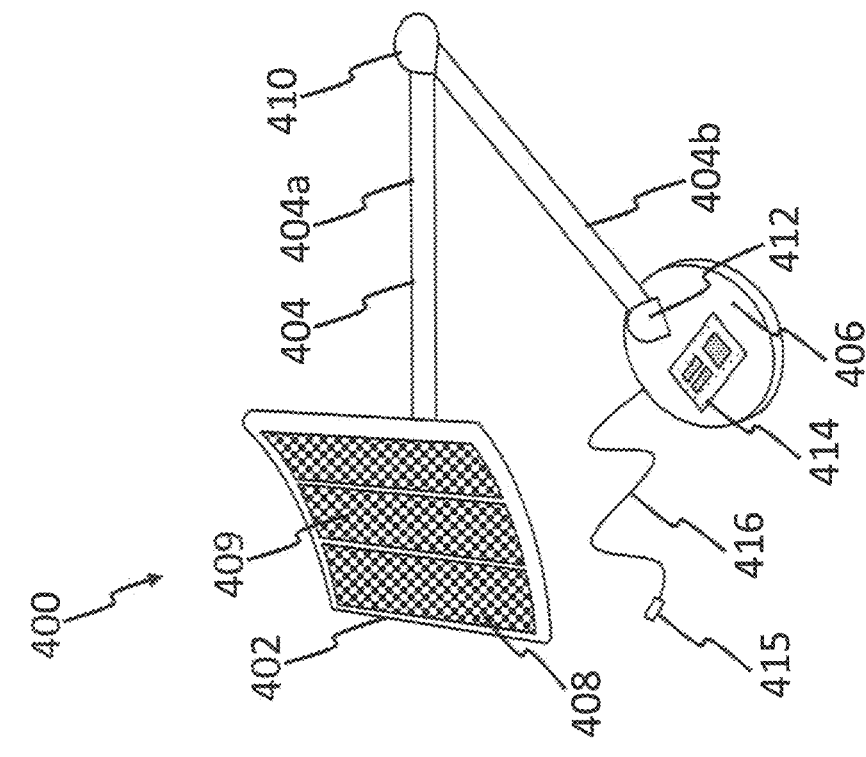
FIG. 14 is an alternative perspective view of the LED panel assembly, showing the LED panel, LED array, extension arms, control unit, power supply, and base plate that mounts to the back wall of the sauna cabin.

FIG. 14 shows an isolated view of the LED panel assembly 400, having an LED panel 402 on an articulated arm system 404 attached to a base 406, further attached to the interior wall of a sauna cabin 101. LED array 408 contains a plurality of individual IR LEDs 409, in quantities that provide sufficient FIR energy 105 for a given application. In a preferred embodiment, LED panel assembly 400 is used in conjunction with multiple FIR heating elements 100 within the same sauna cabin 101.

In a preferred embodiment, due to the use of the arm system 404, user 103 may pull LED panel 402 toward him or her, and position it such that FIR energy 405 emitted from LED panel 402 is concentrated on a specific area of the user's 103 body, such as the face. In a preferred embodiment, LED panel 402 is connected to base 406 by a series of two or more extension arms 404a and 404b that are moveable by way of arm hinge 410 between upper extension arm 404a and lower extension are 404b, and base hinge 412 between lower extension arm 404b and base 406. Arm hinge 410 and base hinge 412 are designed and constructed with sufficient tension such that when user 103 pulls LED panel 402 to the desired position, it remains in place until moved again.

In an embodiment, LED array 404 on LED panel 402 has a user-selectable FIR output, controlled by control unit 414 on base 406. Power to the LED panel assembly 400 is also controlled through control unit 414 and receives power through power adapter 415 and power cord 416 from power receptacle 418 within the sauna cabin 101. Power is supplied from power receptacle 418 (see FIG. 13) through base 406, to LED panel 402 from control unit 414, via electrical conduit (not shown) within extension arms 404a and 404b.

In an alternative embodiment, power to LED panel assembly 400 is supplied through power connections (not shown) that base 406 makes with the wall in sauna 101, removing the requirement for power cord 416 and power receptacle 418. In this embodiment, electrical contacts on both the interior sauna wall (not shown), and electrical contacts (not shown) on the bottom of base 406 complete the power circuit and provide power to LED panel assembly 400 when connected to the sauna wall 102 in sauna cabin 101.

Referring now to FIG. 15, a cut away view of sauna cabin, generally labeled 500, is shown with a bench seat 502 built onto a back wall 504 via hinges 506 below a plurality FIR heating elements 100, of different sizes, also installed in the back wall 504 of sauna 500. Seat base plate 556 of pedestal seat assembly 550 (shown in FIG. 16) is also shown, built into sauna floor 510. Three (3) FIR heating elements 100 are shown in this Figure, however the depicted sauna configuration in this Figure is not intended to be limiting, as additional FIR heating elements may also be installed in any wall of sauna 500 as required. Additionally, sauna 500 may incorporate one or more LED panel assemblies 400

As shown in FIG. 16, at the desire of the user 103, bench seat 502 may be rotated down against back wall 504 via hinges 506. Bench seat 502 is completely out of the way, providing additional space within the sauna 500. In use, bench seat 502 may be secured to side walls 508 with the use of horizontal supports 512. In an alternative embodiment, bench seat 502 is not permanently secured to any of the three walls (back wall 504 and side walls 508), but merely rests on horizontal supports 512 and a back wall support (not shown) that is built into back wall 504. In such an embodiment, the horizontal supports 512 and back wall support (not shown) support the bench seat 502 in use. In this embodiment, the entire bench seat 502 may be lifted off the supports and out of position and stowed vertically against back wall 504 or may be removed from the sauna cabin 500 altogether.

In still another alternative embodiment, bench seat 502 may, instead of rotating down, be rotated up to the vertical and secured to the back wall 504, again moving the bench out of the way. In this alternative embodiment, horizontal supports 512 remain, providing support of either end of bench seat 502 in use, while hinges 506 provide support for bench seat 502 along back wall 504.

Once bench seat 502 is no longer in the way, pedestal seat assembly 550 may be installed in the floor, or more specifically, attached to seat base plate 556 providing a seating solution immediately in front of the FIR heating elements 101. Pedestal seat assembly 550 provides the user with a more comfortable and adjustable seating option than a fixed bench seat. This aspect should not be considered limiting to those skilled in the art, as any number of installation positions may be selected by the user, based on personal preference. Alternatively, the user 103 may also dispense with installation of pedestal seat assembly 550, and utilize the additional floor space within the sauna 500 for stretching or other exercises.

Figure 17:
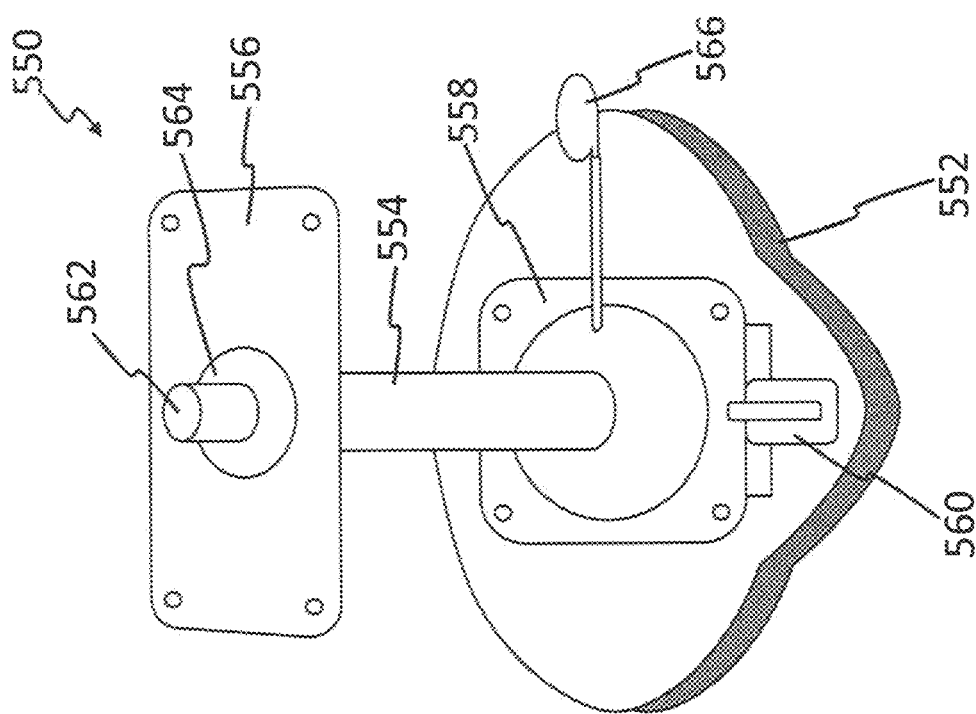
FIG. 17 is a bottom view of the pedestal seat assembly, showing the seat base plate, seat base pole, and seat, further showing the interconnection of the seat base pole and the pedestal seat using a hinge assembly and snap lock.

Referring now to FIG. 17, a bottom perspective view of the pedestal seat assembly, generally labeled 550, is shown, depicting the pedestal seat 552, seat base pole 554, seat base plate 556 and associated hardware. Pedestal seat 552 is connected to seat base pole 554 by way of hinge assembly 558. The hinge assembly's 558 axis lies on the rear of pedestal seat 552, allowing pedestal seat 552 to fold backward, decreasing its overall volume and allowing pedestal seat assembly 550 to be stowed in a more compact manner when not in use. Also shown in FIG. 17 is the snap lock 560, attached to the bottom of pedestal seat 552. Snap lock 560 latches to the hinge base 570 (shown in FIG. 21) when pedestal seat assembly 550 is in use. Releasing snap lock 560 allows pedestal seat 552 to be folded backward as described above.

In a preferred embodiment, seat base pole 554 is formed with a male end 562 that fits securely into barrel 564 (shown in FIG. 15) in seat base plate 556, in use. This feature provides a stable platform for the support of pedestal seat assembly 550 and user 103 in use but also allows easy removal and stowage of pedestal seat assembly 550 when not in use. Additionally, the connection between male end 562 and barrel 564 allows the free rotation of the entire pedestal seat assembly 550, about the male end 562. Snap lock 560 secures hinge assembly 558 in the closed position, as shown, preventing pedestal seat 552 from folding and user 103 from falling backwards off the pedestal seat 552 when seated.

While FIG. 17 depicts a pedestal seat 552 that has a defined "front" and "rear," this should not be considered limiting. Alternative embodiments may employ any practical shape, such as a round pedestal seat.

In order to accommodate various user 103 statures, the preferred embodiment of pedestal seat assembly 550 incorporates a hydraulic cylinder into the seat base pole 554, with height control lever 566, allowing adjustment of seat assembly 550 to various heights. Height control lever 566 is provided to release pressure within the hydraulic cylinder (not shown) to adjust the height of the pedestal seat 552. When user 103 occupies the seat and actuates the height control lever 556, user's 101 bodyweight compresses the cylinder, lowering pedestal seat 552 to the desired height. When user 101 releases height control lever 566, pedestal seat 552 will remain at the selected height, until adjusted further. If the pedestal seat 552 is not occupied and in a low position, when height control lever 556 is actuated the cylinder will extend, raising the pedestal seat 552. This system functions identically to common office chair systems in the market, however in a preferred embodiment, the materials used are selected so as to be compatible with the elevated temperature, sometimes humid sauna environment, and the user's 103 sweat.

Figure 18:
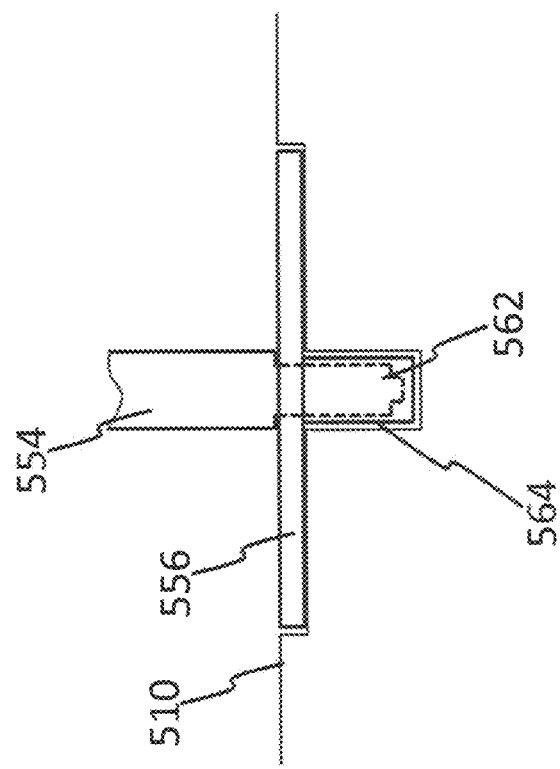
FIG. 18 is a front perspective close up view of the seat pole inserted into the base plate, where the base plate is installed flush with the sauna floor and a hole in the floor to accommodate the barrel mounted to the bottom of the base plate.

FIG. 18 shows the interaction between the seat base pole 554 and seat base plate 556 when user 103 inserts male end 562 into barrel 564. Mounted within the floor 510 of sauna 500 is seat base plate 556 such that the top of the seat base plate 556 is flush with sauna floor 510. Barrel 564 in seat base plate 556 is sized to accommodate male end 562 of seat base pole 554. During construction of the sauna 500, in order to properly install seat base plate 556 in the floor, a hole must first be established in sauna floor 510 to accommodate barrel 564 when seat base plate 556 is installed.

It is to be understood by those skilled in the art that this style of interaction between seat base plate 556 with barrel 564 and male end 562 should not be considered as limiting. In an embodiment, the male end 562 is free to swivel within barrel 564, ultimately allowing the entire pedestal seat assembly 550 to swivel. In an alternative embodiment, the connection between seat base pole 554 and lower hinge plate 568 allows only the pedestal seat 552 to swivel about the seat base pole 554, as opposed to the entire system.

In another alternative embodiment of the pedestal seat assembly 550, male end 562 is formed with a spring-loaded latch (not shown) that secures male end 562 within barrel 564, with a manual release (not shown) formed in the seat base pole 554 for separation of the two elements.

FIG. 19 shows a rear bottom view of the pedestal seat 552 in addition to interaction between the lower hinge plate 568 of the hinge assembly 558 and the seat base pole 554, and the height control lever 566. Also shown is hinge 559 that rotatably connects lower hinge plate 568 to upper hinge plate 569.

Figure 20:
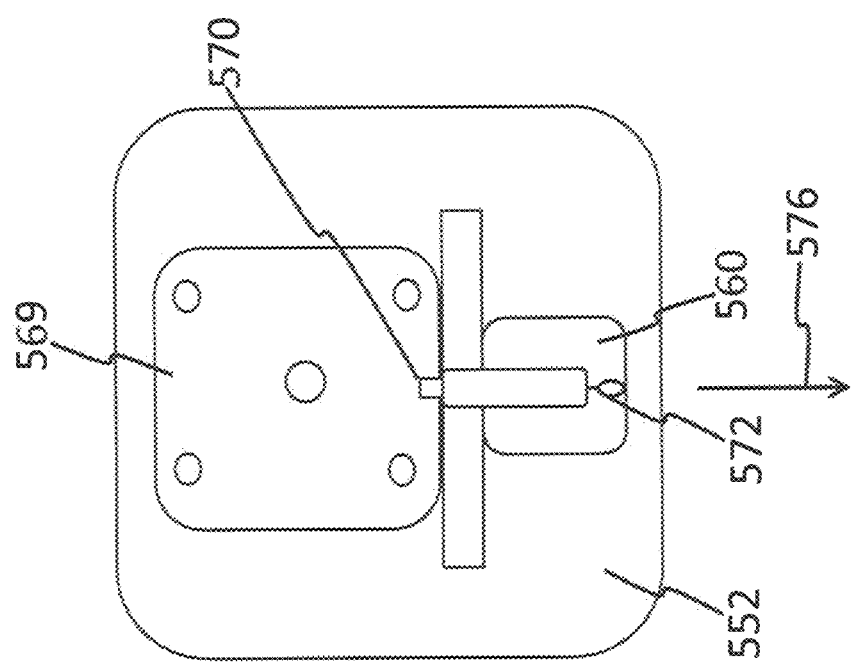
FIG. 20 is a close up view of the snap locking mechanism engaged to keep the hinge in the closed position. Also shown is the release tab that pulls the locking pin back from the base plate thereby allowing the hinge assembly to open.

FIG. 20 shows a close up view of the snap lock 560, in the latched position, on the bottom of pedestal seat 552. In use, latch 570 retains the edge of lower hinge plate 568 and prevents hinge assembly 558 from operating. Snap lock 560 is manipulated by pulling out on tab 572 in direction 576, which in turn pulls in latch 570 and releases the edge of lower hinge plate 568 allowing pedestal seat 552 to rotate away from seat base pole 554 and lower hinge plate 568, as depicted in FIG. 21.

Figure 21:
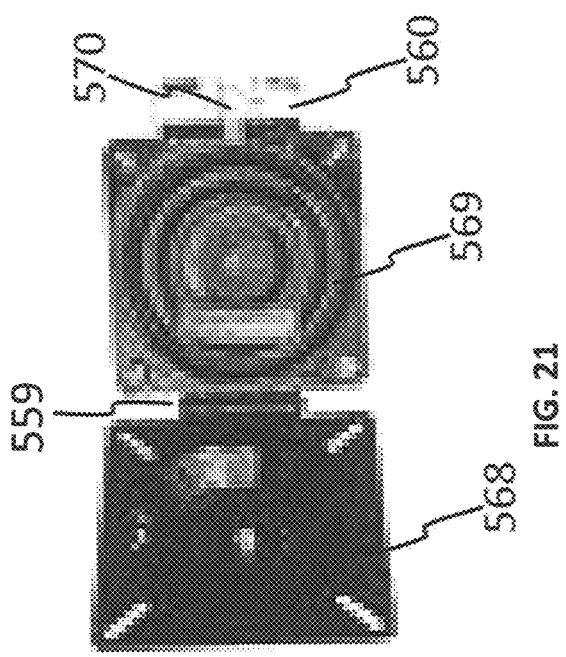
FIG. 21 is a top view of the hinge in operation, as the snap lock is released, and the seat is rotated away from the hinge base and seat base pole.

Referring now to FIG. 21, hinge assembly 558 is shown in the open position, after snap lock 560 has been actuated, isolated from pedestal seat 552 and the seat base pole 554. Lower hinge plate 568 is attached to the top of seat base pole 554, while upper hinge plate 574 is fastened to the bottom of pedestal seat 502 by way of hardware fasteners, such as bolts or screws (not shown). Provisions for four such fasteners on both upper hinge plate 574 and lower hinge plate 568 are depicted in this Figure, however that should not be interpreted as limiting by those skilled in the art. This configuration of pedestal seat assembly 550 allows for the folding of pedestal seat 552 and easier stowage of pedestal seat assembly 550, such as under the bench seat 502 in sauna 500 in FIG. 15 and FIG. 16.

It should be appreciated by those skilled in the art, that any such latch or similar locking mechanism like snap lock 560 may be employed to prevent pedestal seat 552 from rotating and allowing pedestal seat assembly 550 from folding. In an embodiment, hinge assembly 558 incorporates a locking mechanism into the design of the hinge itself, eliminating the requirement for a separate latching mechanism, such as snap lock 560.

Figure 22:
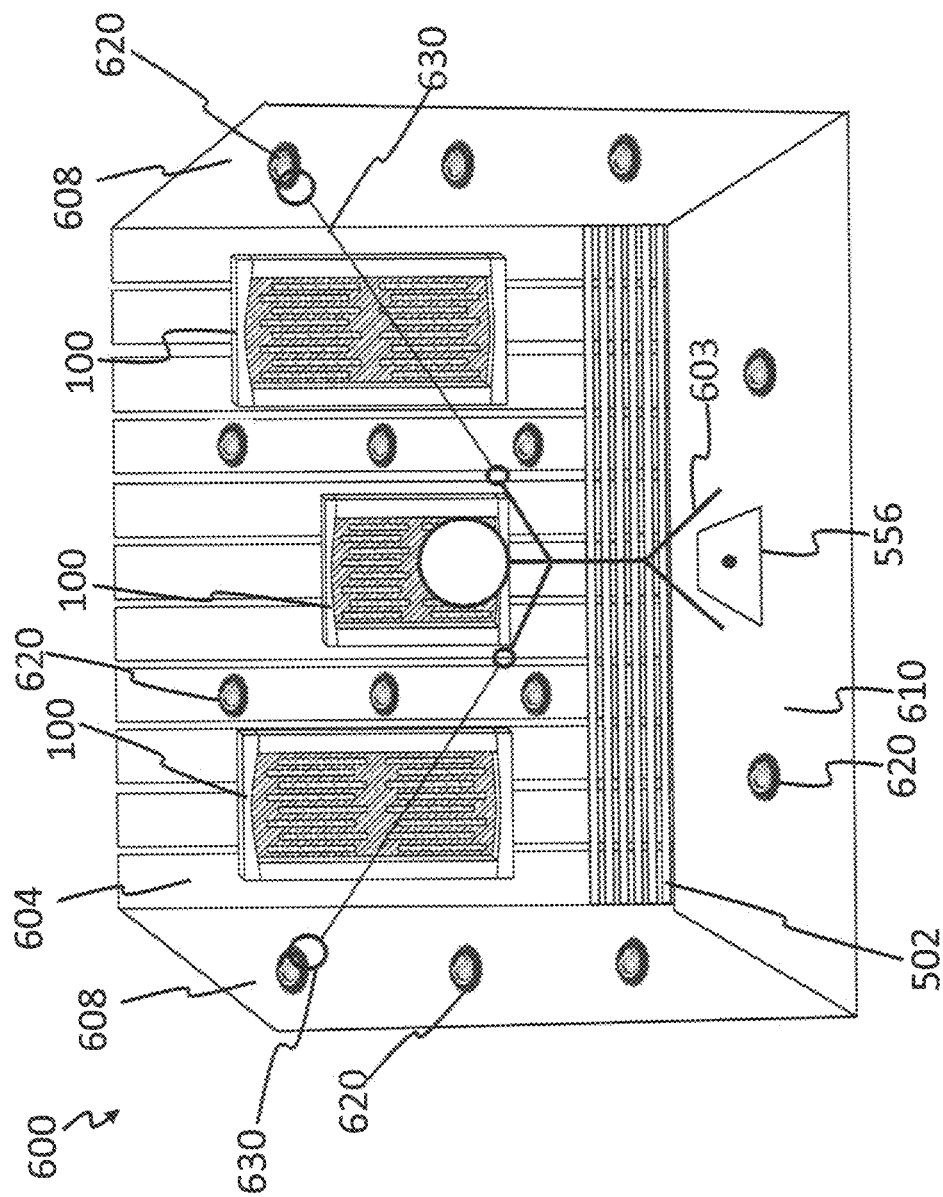
FIG. 22 is a perspective, cut away view of the interior of a sauna cabin back wall, side wall, floor, showing the slotted front of the carbon panel with the enclosure built around the face of the FIR heating element. Also shown is the "D" ring assembly installed in multiple locations in each panel of the interior of the sauna cabin.

Referring now to FIG. 22, a cutaway of the interior of an exemplary exercise sauna 600, showing three FIR heating elements 100 installed in the back wall 604, similar to FIG. 15 and FIG. 16. In addition to the other features of previous Figures, multiple "D" rings 620 are installed in the back wall 604 and side walls 608, and sauna floor 610. Also pictured is seat base plate 556 installed in sauna floor 610. Further, and similar to previous embodiments, bench seat 502 is also shown in the stowed position against back wall 604, providing additional space to user 603 within sauna cabin 600.

"D" rings 620 are designed to provide a fixed point to which exercise implements such as elastic bands 630 or other similar exercise implements may be attached for use while user 603 is inside the sauna. In this Figure, user 603 is depicted working out with two elastic bands 630 attached to back wall 604. In a preferred embodiment, any number of different exercises may be accomplished through resistance training with elastic bands 630, making use of the various "D" ring 620 positions within sauna 600. While the user 603 is inside the sauna cabin, he may take advantage of "D" rings 620 and elastic bands 630 through various arm exercises such as a modified bench press, military press, or innumerable shoulder, core, and arm exercises. By using the floor 610 mounted "D" rings 620, overhead exercises may also be performed, in addition to leg and core exercises.

By conducting a workout within the confines of a sauna 600, user 603 gains the benefit not only of the resistance training, but also the FIR energy 105 he or she absorbs while inside sauna 600. The physical exertion of a workout plus the FIR energy 105 produces a much heavier sweat benefitting the user 603 significantly more than exercise alone.

Also shown in FIG. 22 is the seat base plate 556. This Figure is exemplary of the additional room afforded the user 603 when bench 502 is in the stowed position and pedestal seat assembly 550 is removed. The extra space provided allows the user 603 to conduct many variations of exercise or stretching, hot yoga, resistance training, or other such activities. In an alternative preferred embodiment, user 603 may also install pedestal seat assembly 550 (not shown) using it as support or to further vary the exercise possibilities within sauna 600. "D" rings 620 are shown in several locations on all walls of sauna 600, indicative of the versatility and varying options for connection and use of elastic exercise bands 630.

FIG. 23 is a close up view of the back wall 604 of sauna 600. FIR heating element 100 is installed in back wall 604, and six (6) "D" rings 620 are shown, fastened to back wall 604, between FIR heating elements 100. It is to be appreciated by those skilled in the art that the six "D" rings 620 depicted should not be considered limiting and more or fewer may be installed to optimize or customize the interior of sauna 600. Virtually any number of "D" rings 620 may be installed at the user 603's discretion, providing additional exercise options. The same options exist for the side walls 608 and floor 610.

Referring now to FIG. 24, an exploded view of the "D" ring fastener 620 is shown. In a preferred embodiment, the "D" ring 620 has a protective grommet 622, ring 624, and bracket 626. Protective grommet 622 is in a position between the wall 604 of sauna 600 and bracket 626, secured to wall 604 by way of screws, bolts, and any other hardware typical of this type of installation. Protective grommet 622 is intended to provide a surface against which ring bracket 624 rests, and protection against any damage to wall 604 that might otherwise be caused by clips or fasteners attached to the ring 624 during a user's 603 exercise routine.

Ring 624 and bracket 626 are integrated parts, in which ring 624 is capable of rotation along an axis perpendicular to the plane of the bracket 626. This enables the ring 624 to fold flat against grommet 622 when ring 624 is not in use. "D" ring 620 provides a connection point for elastic bands 630 or other similar exercise implements desired by the user 603. In a preferred embodiment, the "D" ring 624 is mounted in such a way that the ring 626 will fall flat against the grommet 622 when not in use.

Figure 25:
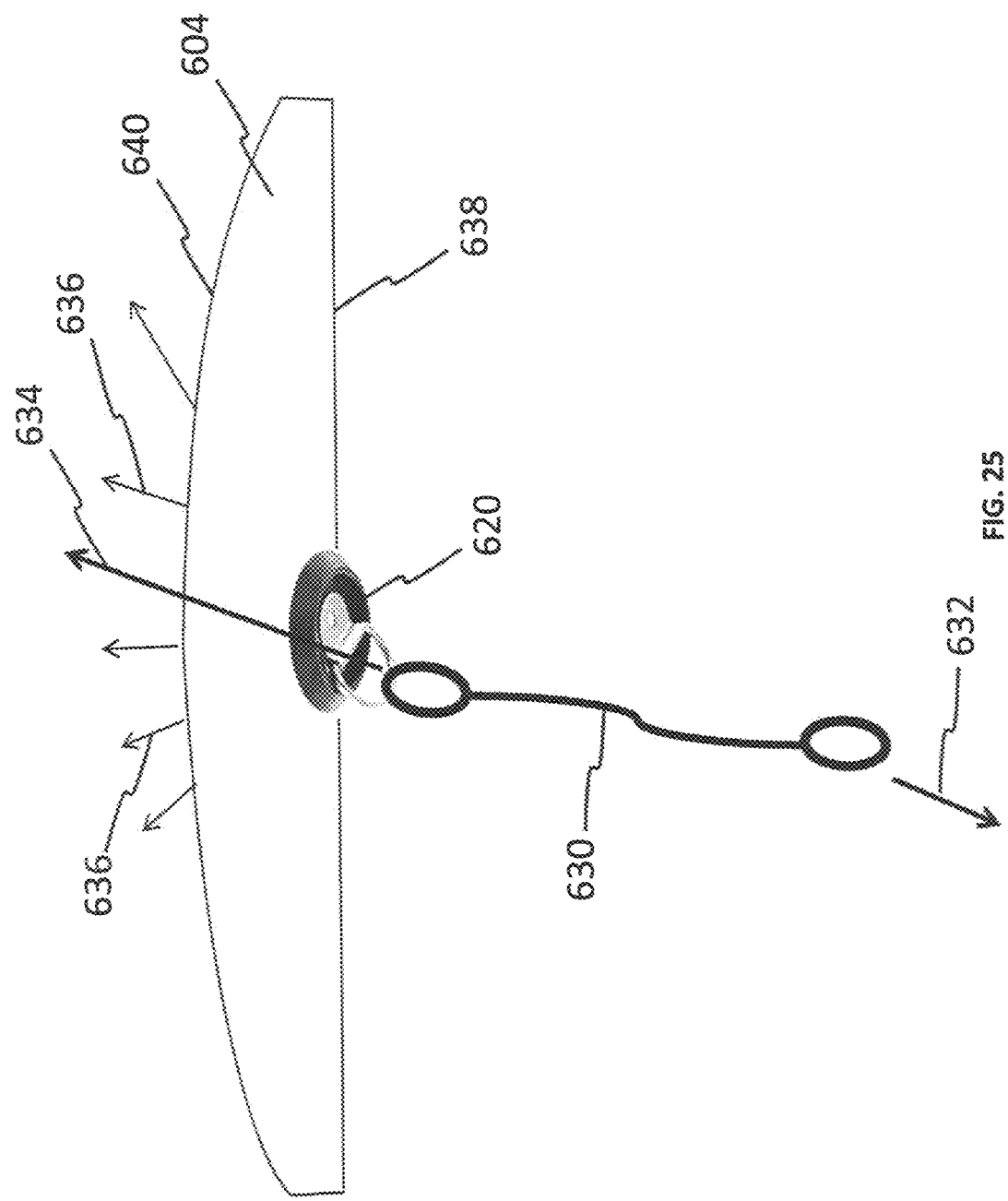
FIG. 25 is a cross sectional view of the construction of a preferred embodiment of the externally curved sauna cabin wall, showing the interaction of the "D" rings as installed in addition to the forces acting on the curved outer sauna walls.

Referring now to FIG. 25, a top view of a back wall 604 with a "D" ring 620 installed and an elastic exercise band 630 attached to the "D" ring 630. Due to the curvature of the outer portion 640 of back wall 604, when a user 603 (not shown) applies a force to elastic exercise band 630 in direction 630, an equal and opposite force is also applied in direction 634. The equal and opposite force is then distributed along the curve formed by outer portion of the back wall 604 in direction 636. Forces 634 such as these are not typical for sauna construction, and as such, certain modifications to the structure are beneficial. A force 634 such as that described above acting perpendicular to flat inner wall portion 638 may tend to flex the wall inward in direction 632, bowing the wall 604 and potentially causing damage to the structure with time. However in the preferred embodiment of sauna 600 with "D" rings 620 installed, as shown by FIG. 25, sauna walls 609 employ a curvature of the outer wall portions, such as outer wall portion 634 of back wall 604. This external curvature of the outer sauna wall 609 more effectively distributes the forces imparted on the inner wall portion 638 of back wall 604. Much like an arch distributes the weight of the bridge or building for which it was built, the external curves more evenly distribute force 634 into smaller force components 640 and prevent the inward bowing that would otherwise be experienced without the use of an externally curved sauna wall 609, using the "D" rings 620 in sauna 600. In use, externally curved wall 609 may be utilized in place of sauna back wall 604 or side wall 608, or corresponding features of other, previously describe embodiments. It is to be appreciated by someone skilled in the art that one or more walls may have a curved out portion depending on the design of a spa and the needs of the user.

While there have been shown what are presently considered to be preferred embodiments of the present invention, it will be apparent to those skilled in the art that various changes and modifications can be made herein without departing from the scope and spirit of the invention.

I claim:

1. A sauna, comprising:
   a sauna cabin having a floor, a ceiling, and at least three walls extending between said floor and said ceiling to form an enclosure, wherein each of the at least three walls have a planar interior surface and a curved exterior surface;
   one or more heating elements;
   a seat;
   a plurality of attached mechanisms located on the floor and the floor and the interior surface of the at least three walls, the attached mechanisms configured to receive a connector of an exercise implement; and
   D-rings attached to said attached mechanisms.

2. The sauna of claim 1 wherein said heating element further comprises a far infrared heating element.

3. The sauna of claim 2 wherein said far infrared heating element emits radiation in the far infrared electromagnetic spectrum.

4. The sauna of claim 1 wherein said heating element further comprises a ceramic heating element.

5. The sauna of claim 4 wherein said ceramic heating element emits radiation in the far infrared electromagnetic spectrum.

6. The sauna of claim 1, wherein said one or more heating elements further comprises a carbon panel.

7. The sauna of claim 6, further comprising a backing layer adjacent said carbon panel.

8. The sauna of claim 6, wherein said carbon panel further comprises a metal shroud adjacent said carbon panel and formed with one or more slots through which heat from said carbon panel passes into said cabin.

9. The sauna of claim 1 further comprising a light emitting diode radiation source.

10. The sauna of claim 9, wherein said light emitting diode radiation source extends from said wall and is positionable within said enclosure.

11. The sauna of claim 1, wherein said D-rings comprise rotatably attached D-rings.

12. The sauna of claim 1, wherein said seat is a pedestal seat.

13. The sauna of claim 12, wherein said pedestal seat further comprises:
   a seat base plate secured to said floor; and
   a seat base pole extending from said seat base plate to said seat; wherein said pedestal seat is configurable between a first position installed in said seat base plate, and a second position removed from said seat base plate.

14. The sauna of claim 1, wherein said seat a bench seat.

15. The sauna of claim 14, wherein said bench seat further comprises:
   a bench seat surface extending from a wall; wherein said bench seat surface is configurable between a first horizontal position perpendicular from said wall, and a second vertical position substantially parallel to said wall.

16. The sauna of claim 1, further comprising one or more exercise bands removably attached to said plurality of attached mechanisms on said ceiling.

17. The sauna of claim 1, wherein said plurality of attached mechanisms further comprises attached mechanisms on said ceiling.

18. A sauna, comprising:
   a sauna cabin having a floor, a ceiling, and at least three walls extending between said floor and said ceiling to form an enclosure, wherein each of the at least three walls have a planar interior surface and a curved exterior surface;
   a seat;

a plurality of attached mechanisms located on the floor and the at least three walls, the attached mechanisms configured to receive an exercise implement;

D-rings attached to said attached mechanisms; and at least one ceramic heating element;

at least one carbon panel; and a metal shroud adjacent said ceramic heating element to reflect infrared heat energy from the ceramic heating elements toward said seat.

19. The sauna of claim 18, wherein said metal shroud is formed with one or more slots through which heat from said carbon panel passes.

20. The sauna of claim 19, wherein said carbon panel comprises two or more heating layers.

* * * * *

UNITED STATES PATENT AND TRADEMARK OFFICE
CERTIFICATE OF CORRECTION

PATENT NO. : 9,629,777 B2
APPLICATION NO. : 13/933018
DATED : April 25, 2017
INVENTOR(S) : David Floyd Shurtleff It is certified that error appears in the above-identified patent and that said Letters Patent is hereby corrected as shown below:

In the Claims

Column 18, Line 47, change "wherein said seat a bench seat" to -wherein said seat is a bench seat- Signed and Sealed this
Thirtieth Day of May, 2017

Michelle K. Lee
*Director of the United States Patent and Trademark Office*